United States Patent
Potyrailo et al.

(10) Patent No.: US 6,763,322 B2
(45) Date of Patent: Jul. 13, 2004

(54) METHOD FOR ENHANCEMENT IN SCREENING THROUGHPUT

(75) Inventors: Radislav Alexandrovich Potyrailo, Niskayuna, NY (US); Ronald Eugene Shaffer, Clifton Park, NY (US)

(73) Assignee: General Electric Company, Nishayuna, NY (US)

( * ) Notice: Subject to any disclaimer, the term of this patent is extended or adjusted under 35 U.S.C. 154(b) by 209 days.

(21) Appl. No.: 10/040,420

(22) Filed: Jan. 9, 2002

(65) Prior Publication Data

US 2003/0130823 A1 Jul. 10, 2003

(51) Int. Cl.[7] .......................... G06F 15/00; H04B 15/00
(52) U.S. Cl. ....................... 702/189; 702/127; 702/176; 378/4
(58) Field of Search ............................ 702/19–32, 108, 702/109, 127, 176, 179, 182, 183, 184–191, 193, 194; 250/281, 282, 287, 339.09; 378/901, 4

(56) References Cited

U.S. PATENT DOCUMENTS

| | | | |
|---|---|---|---|
| 3,615,454 A | * 10/1971 | Cescon et al. | 430/292 |
| 4,780,859 A | 10/1988 | Hadidi et al. | 367/43 |
| 5,000,183 A | 3/1991 | Bonnefous et al. | 600/437 |
| 5,115,812 A | * 5/1992 | Sano et al. | 600/419 |
| 5,436,447 A | 7/1995 | Shew | 399/1 |
| 5,497,777 A | * 3/1996 | Abdel-Malek et al. | 600/443 |
| 5,528,725 A | 6/1996 | Hui | 704/236 |
| 5,561,431 A | 10/1996 | Peele et al. | 342/90 |
| 5,587,931 A | 12/1996 | Jones et al. | 702/34 |
| 5,619,998 A | * 4/1997 | Abdel-Malek et al. | 600/437 |
| 5,638,823 A | 6/1997 | Akay et al. | 600/528 |
| 5,667,244 A | 9/1997 | Ito et al. | 280/735 |
| 5,671,330 A | 9/1997 | Sakamoto et al. | 704/268 |
| 5,704,357 A | * 1/1998 | Miyazaki et al. | 600/410 |
| 5,740,036 A | * 4/1998 | Ahuja et al. | 702/17 |
| 5,885,841 A | 3/1999 | Higgs, Jr. et al. | 436/89 |
| 5,923,785 A | 7/1999 | Dube | 382/240 |
| 6,031,609 A | * 2/2000 | Funk et al. | 356/310 |
| 6,094,050 A | 7/2000 | Zaroubi et al. | 324/309 |
| 6,103,350 A | * 8/2000 | Grangeat et al. | 428/195.1 |

(List continued on next page.)

FOREIGN PATENT DOCUMENTS

SU 587468 A * 2/1978 ........... G06F/15/36

OTHER PUBLICATIONS

Beebe, K. R. et al. Cemometrics: A Practical Guide, 1998. Wiley–Interscience Publication, pp. 6, 278–280.*

Vandeginste, B.G.M., Massart, D.L., Buydens, L.M.C., Dejong, S., Lewi, P.J., and Smeyers–Verbeke, J., Handbook of Chemometrics and Qualimetrics, Part B., Elsevier, Amsterdam, The Netherlands, pp. 535–553, 1998.

Alsberg, B. K.; Woodward, A. M.; Kell, D. B., An introduction to wavelet transforms for chemometricians: a time–frequency approach, Chemom. Intell. Lab. Syst., 1997, 37, 215–239.

(List continued on next page.)

*Primary Examiner*—Marc S. Hoff
*Assistant Examiner*—Manuel L. Barbee
(74) *Attorney, Agent, or Firm*—Andrew J. Caruso; Patrick K. Patnode

(57) ABSTRACT

The present invention provides methods and an apparatus for the rapid analysis of data from imaging, spectroscopic, scanning probe, or sensor methods. By application of mathematical transform analysis such as wavelet transform algorithms to one or multi-order data sets obtained from individual samples or sample arrays, the analytical features of the data are preserved while undesired noise is removed, thereby reducing the integration time by more than 10-fold in subsequent measurements. The reduction in integration time enables the high-throughput measurement of combinatorial libraries and rapid dynamic processes, while still providing a signal-to-noise level suitable for a reliable measurement.

37 Claims, 12 Drawing Sheets

U.S. PATENT DOCUMENTS

| | | | |
|---|---|---|---|
| 6,108,609 A | 8/2000 | Qian et al. | 702/66 |
| 6,119,026 A | 9/2000 | McNulty et al. | 600/310 |
| 6,208,951 B1 | 3/2001 | Kumar et al. | 702/191 |
| 6,253,162 B1 | 6/2001 | Jarman et al. | 702/179 |
| 6,411,089 B1 * | 6/2002 | Anand et al. | 324/309 |
| 2001/0053958 A1 * | 12/2001 | Ried et al. | 702/19 |
| 2002/0002331 A1 * | 1/2002 | Cline et al. | 600/410 |
| 2002/0171422 A1 * | 11/2002 | King | 324/307 |

OTHER PUBLICATIONS

Amara, IEEE Computational Sciences and Engineering, 1995, 2, 50–61.

Antoine, J.–P.; Chauvin, C.; Coron, A. Wavelets and related time–frequency techniques in magnetic resonance spectroscopy. NMR Biomed., 2001, 14(4), 265–270.

Artursson, Tom; Hagman, Anders; Bjork, Seth; Trygg, Johan; Wold, Svante; Jacobsson, Sven P. Study of preprocessing methods for the determination of crystalline phases in binary mixtures of drug substances by X–ray powder diffraction and multivariate calibration. Appl. Spectrosc., 2000, 54(8), 1222–1230.

Barclay, V. J.; Bonner, R. F.; Hamilton, I. P. Application of Wavelet Transforms to Experimental Spectra: Smoothing, Denoising, and Data Set Compression. Anal. Chem., 1997, 69(1), 78–90.

Beebe, K. R., Pell, R. J., and Seasholtz, M. B., Chemometrics: A Practical Guide, 1998, pp. 6, 279, Wiley, New York, NY.

Bos, M.; Hoogendam, E., Wavelet transform for the evaluation of peak intensities in flow–injection analysis, Anal. Chim. Acta, 1992, 267, 73–80.

Bos, M.; Vrielink, J. A. M., The wavelet transform for pre–processing IR spectra in the identification of mono– and di–substituted benzenes, Chemom. Intell. Lab. Syst., 1994, 23, 115–122.

C. L. Philips and J. M. Parr, Signals, Systems, and Transforms, 1999, pp. 2, 174, 289, 390, Prentice Hall, Upper Saddle River, NJ.

Cai, Chunsheng; de Harrington, Peter. Different discrete wavelet transforms applied to denoising analytical data. J. Chem. Inf. Comput. Sci., 1998, 38(6), 1161–1170.

Cai, Wensheng; Wang, Liya; Pan, Zhongxiao; Zuo, Jian; Xu, Cunyi; Shao, Xueguang. Application of the wavelet transform method in quantitative analysis of Raman spectra. J. Raman Spectrosc., 2001, 32(3), 207–209.

Chau, F. T.; Shih, T. M.; Gao, J. B.; Chan, C. K., Application of the fast wavelet transform method to compress ultraviolet–visible spectra, Appl. Spectrosc., 1996, 59, 339–348.

D. A. Skoog and G. G. Leary, Principles of Instrumental Analysis, 4$^{th}$ Ed., Saunders College Publishing, Fort Worth, TX, 1992, p. 592.

Depczynski, U.; Jetter, K.; Molt, K.; Neimoller, A. The fast wavelet transform on compact intervals as a tool in chemometrics II. Boundary effects, denoising and compression. Chemom. Intell. Lab. Syst., 1999, 49(2), 151–161.

Donoho, D., Different perspectives on Wavelets, Proceedings of Symposia in Applied Mathematics, 1993, 47, 173–205.

Einax, J. W.; Zwanziger, H. W.; Geiss, S. Chemometrics in Environmental Analysis, 1997, p. 164, VCH, Weinheim.

Estienne, F.; Massart, D. L.; Zanier–Szydlowski, N.; Marteau, P. Multivariate calibration with Raman spectroscopic data: a case study. Chim. Acta, 2000, 424(2), 185–201.

F. Ehrentreich and L. Summchen. Spike Removal and Denoising of Raman Spectra by Wavelet Transform Methods, Analytical Chemistry, 2001, in press.

Gunther, Ulrich L.; Ludwig, Christian; Ruterjans, H. NMR-LAB–Advanced NMR Data Processing in Matlab. J. Magn. Reson., 2000, 145(2), 201–208.

Hierlemann, A., Schweizer–Berberich, M., Weimar, U., Kraus, G., Pfau, A., and Göpel, W., In Sensors Update, vol. 2; Eds., H. Baltes, W. Göpel, and J. Hesse, VCH, Weinheim, 1996, pp 119–180.

Jetter, K.; Depczynski, U.; Molt, K.; Neimoller, A. Principles and applications of wavelet transformation to chemometrics. Anal. Chim. Acta, 2000, 420(2), 169–180.

Jouan–Rimbaud, D.; Walczak, B.; Poppi, R. J.; de Noord, O. E.; Massart, D. L., Application of wavelet transform to extract the relevant component from spectral data for multivariate calibration, Anal. Chem., 1997, 69, 4317–4323.

Leung, Alexander Kai–Man; Chau, Foo–Tim; Gao, Jun–Bin. A review on applications of wavelet transform techniques in chemical analysis: 1989–1997. Chemom. Intell. Lab. Syst., 1998, 43(1,2), 165–184.

Mao, Jun Jun; Sun, Pei Yan; Pan, Zhong Xiao; Su, Qing De. Wavelet analysis on photoacoustic spectra of degraded PVC. Fresenius' J. Anal. Chem., 1998, 361(2), 140–142.

Martens, H.; Martens, M., Multivariate Analysis of Quality. An Introduction; Wiley: Chichester, England, 2001, p 5–6.

McQuay, James. A.; Karanassios, Vassili. Wavelet de–noising of transient signals generated from micro–samples and ITV–ICP–AES and comparison with digital filtering obtained using fast Fourier– and fast Hartley–transforms. Can. Editor(s): Clement, Ray; Burk, Bob. EnviroAnal. 2000, Proc. Bienn. Int. Conf. Monit. Meas. Environ., 3rd 2000, 149–154, Publisher: EnviroAnalysis 2000 Conference secretariat, Ottawa, Ont.

Mittermayr, C. R.; Lendl, B.; Rosenberg, E.; Grasserbauer, M. The application of the wavelet power spectrum to detect and estimate 1/f noise in the presence of analytical signals. Anal. Chim. Acta, 1999, 388(3), 303–313.

Mittermayr, C. R.; Nikolov, S. G.; Hutter, H.; Grasserbauer, M., Wavelet denoising of Gaussian peaks: a comparative study, Chemom. Intell. Lab. Syst., 1996, 34, 187–202.

Naes, T.; Isaksson, T.; Kowalski, B., Locally weighted regression and scatter correction for near–infrared reflectance data, Analytical Chemistry, 1990, 62, 664–673.

Nikolov, S. G.; Hutter, H.; Grasserbauer, M., De–noising of SIMS images via wavelet shrinkage, Chemom. Intell. Lab. Syst. 1996, 263–273.

Otto, M. Chemometrics: Statistics and Computer Application in Analytical Chemistry, 1999, p. 215, Wiley–VCH, Weinheim, Germany.

P.J. Treado and M.D. Morris, A Thousand Points of Light: The Hadamard Transform in Chemical Analysis and Instrumentation, Analytical Chemistry, 1989, 61, 723A–734A.

Pasti, L.; Walczak, B.; Massart, D. L.; Reschiglian, P. Optimization of signal denoising in discrete wavelet transform. Chemom. Intell. Lab. Syst., 1999, 48(1), 21–34.

Ren, Shouxin; Gao, Ling. Simultaneous quantitative analysis of overlapping spectrophotometric signals using wavelet multiresolution analysis and partial least squares. Talanta, 2000, 50(6), 1163–1173.

Roy, Manojit; Kumar, V. Ravi; Kulkarni, B. D.; Sanderson, John; Rhodes, Martin; Stappen, Michel vander. Simple denoising algorithm using wavelet transform. AIChE J., 1999, 45(11), 2461–2466.

Sadler, D. A.; Boulo, P. R.; Soraghan, J. S.; Littlejohn, D. Tutorial guide to the use of wavelet transforms to determine peak shape parameters for interference detection in graphite–furnace atomic absorption spectrometry. Spectrochim. Acta, Part B, 1998, 53B(6–8), 821–835.

Sadler, D. A.; Littlejohn, D.; Boulo, P. R.; Soraghan, J. S. Application of wavelet transforms to determine peak shape parameters for interference detection in graphite–furnace atomic absorption spectrometry. Spectrochim. Acta, Part B, 1998, 53B(6–8), 1015–1030.

Savitsky, A. and M. Golay, Smoothing and Differentiation of Data using Simplified Least–Squares Procedures, Analytical Chemistry, 1964, 36, 1627–1639.

Shao, Xue Guang; Li, Wan; Chen, Gang; Su, Qing De. Online analysis of the photoacoustic spectral signal using wavelet transform. Fresenius' J. Anal. Chem., 1999, 363(3), 215–218.

Shao, Xueguang; Cai, Wensheng. A novel algorithm of the wavelet packets transform and its application to de–noising of analytical signals. Anal. Lett., 1999, 32(4), 743–760.

Shao, Xueguang; Cai, Wensheng. Wavelet analysis in analytical chemistry. Rev. Anal. Chem., 1998, 17(4), 235–285.

Shao, Xueguang; Cai, Wensheng; Pan, Zhongxiao. Wavelet transform and its applications in high performance liquid chromatography (HPLC) analysis. Chemom. Intell. Lab. Syst., 1999, 45(1,2), 249–256.

Shao, Xueguang; Hou, Shuquan. An on–line wavelet transform for de–noising of high performance liquid chromatograms. Anal. Lett., 1999, 32(12), 2507–2520.

Shao, Xueguang; Pang, Chunyan; Su, Qingde. A novel method to calculate the approximate derivative photoacoustic spectrum using continuous wavelet transform. Fresenius' J. Anal. Chem., 2000, 367(6), 525–529.

Shao, Xueguang; Sun, Li. An application of the continuous wavelet transform to resolution of multicomponent overlapping analytical signals. *Anal. Lett.,* 2001, 34(2), 267–280.

Shao, Xueguang; Yu, Fang; Kou, Hongbing; Cai, Wensheng; Pan, Zhongxiao. A wavelet–based genetic algorithm for compression and de–noising of chromatograms. Anal. Lett., 1999, 32(9), 1899–1915.

Shao, Xueguang; Gu, Hua; Wu, Jihui; Shi Yunyu. Resolution of the NMR spectrum using wavelet transform. Appl. Spectrosc., 2000, 54(5), 731–738.

Smrcok, Lubomir; Durik, Marian; Jorik, Vladimir. Wavelet denoising of powder diffraction patterns. Powder Diffr., 1999, 14(4), 300–304.

Sternickel, Karsten; Effern, Arndt; Lehnertz, Klaus; Schreiber, Thomas; David, Peter. Nonlinear noise reduction using reference data. Phys. Rev. E: Stat., Nonlinear, Soft Matter Phys., 2001, 63(3–2), 036209/1–036209/4.

T. Masters, *Signal and Image Processing With Neural Networks. A C++ Sourcebook,* 1994, p. 150, Wiley, New York, NY.

Teppola, Pekka; Minkkinen, Pentti. Wavelets for scrutinizing multivariate exploratory models—interpreting models through multiresolution analysis. Chemometrics Group, Laboratory of Inorganic and Analytical Chemistry, J. Chemom., 2001, 15(1), 1–18.

Thompson, Robert Q., Experiments in Software Data Handling, Journal of Chemical Education, 1985, 62, 866–869.

Walczak, B.; Bouveresse, E.; Massart, D. L., Standardization of near–infrared spectra in the wavelet domain, *Chemom. Intell. Lab. Syst.* 1997, 36, 41–51.

Walczak, B.; Massart, D. L., Noise suppression and signal compression using the wavelet packet transform, *Chemom. Intell. Lab. Syst.*, 1997, 36, 81–94.

Walczak, B.; Massart, D. L., Wavelets—something for analytical chemistry?, *Trends Anal. Chem.,* 1997, 16, 451–463.

Walczak, B.; van den Bogaert, B.; Massart, D. L., Application of wavelet packet transform in pattern recognition of near–IR data, *Anal. Chem.,* 1996, 68, 1742–1747.

Wolkenstein, M.; Stubbings, T.; Hutter, H. Robust automated three–dimensional segmentation of secondary ion mass spectrometry image sets. Fresenius' J. Anal. Chem., 1999, 365(1–3), 63–69.

Young, K.; Soher, B. J; Maudsley, A. A., Automated spectral analysis II: Application of wavelet shrinkage for characterization of non–parameterized signals, *Magn. Reson. Med.,* 1998, 40, 816–821.

* cited by examiner

US 6,763,322 B2

METHOD FOR ENHANCEMENT IN SCREENING THROUGHPUT

BACKGROUND OF THE INVENTION

This invention relates to rapid throughput screening of combinatorial libraries. More particularly, the invention relates to methods and devices for reducing data acquisition time for spectroscopic analysis and imaging of multiple samples.

From the analytical perspective, quantification of a chemical property requires that the data can be analyzed with high confidence that any variation in the measured signal is due to a change of a chemical property of the sample, and not to variation in the measurement system. The quality of analysis of samples from combinatorial libraries is determined by a number of factors, the most important of which are the speed of measurement (screening throughput), reproducibility (precision), and accuracy. Precision generally will improve as the measured quantity due to the parameter of interest (signal) increases in comparison to the measured quantity due to general background (noise). For a variety of analytical techniques, increasing signal integration time improves signal quality. For high throughput screening of large numbers of samples, however, increasing integration time is often impractical.

Also, in many cases, the measured signal is proportional to sample size. For example, in Raman and fluorescence spectroscopy, the measured signal is directly proportional to the illuminated sample volume. Similarly, in absorption, mass-spectrometric, ionization, gravimetric, and other types of detection systems, the sample must be large enough to provide a detectable change in instrument response. However, developing new products and processes often requires combinatorial approaches that utilize multiple small-scale reactions arranged in an array format. Although efficient from the standpoint of cost, the small sample size is often accompanied by a decrease in signal, thus requiring long data acquisition times per sample.

Although many analytical techniques can be used to analyze libraries of small individual samples, these detection schemes are generally not practical because of the long sample integration times needed to analyze small samples. Thus, there is a need to develop a method by which signal integration time, and therefore overall data acquisition time, is reduced to a point where it no longer limits methods of analysis.

SUMMARY OF THE INVENTION

The present invention comprises methods and devices for reducing sample integration time using mathematical transform analysis and, thereby, significantly reducing the time required for screening multiple samples. The invention is particularly suited for screening combinatorial libraries comprising multiple samples of small volume.

In one aspect, the invention comprises a method for reducing the time required for analyzing at least one sample for a parameter of interest which comprises collecting analytical data from a sample using a predetermined integration time $T_a$ and applying mathematical transform analysis on the data, wherein the mathematical transform analysis is performed using conditions designed to achieve a pre-determined signal quality response function value comprising the value obtained when samples are analyzed without mathematical transform analysis using integration time $T_b$, wherein $T_b$ is greater than $T_a$.

In another aspect, the invention comprises an apparatus for analyzing at least one sample for a parameter of interest using a pre-determined signal quality response function which comprises: a collecting system for collecting analytical data comprising the parameter of interest from a sample; a processing system for processing the analytical data; a screening rate accelerator toolbox for applying mathematical transform analysis to the data; a data analysis system for determining whether the data processed by the screening rate accelerator toolbox satisfies a pre-determined signal quality response function value; and a statistical toolbox for analyzing the processed data for the parameter of interest.

The foregoing focuses on the more important features of the invention in order that the detailed description which follows may be better understood and in order that the present contribution to the art may be appreciated. There are additional features of the invention which will be described hereinafter and which will form the subject matter of the claims appended hereto. It is to be understood that the invention is not limited in its application to the details as set form in the following description and drawings, but is capable of other embodiments and of being practiced or carried out in various ways.

BRIEF DESCRIPTION OF THE DRAWINGS

Various features, aspects and advantages of the present invention will become more apparent with reference to the following description, appended claims, and accompanying drawings, wherein:

Figure 10:
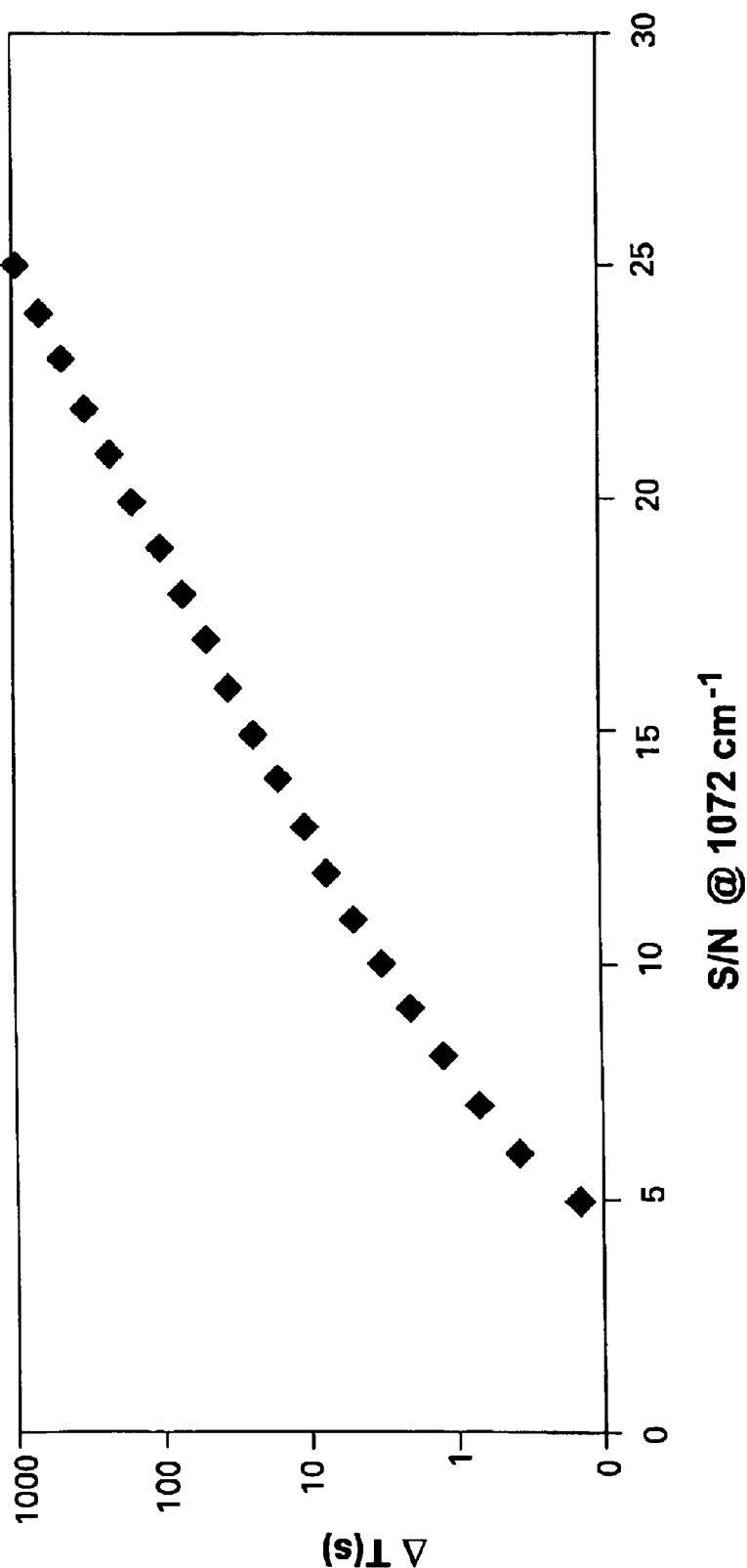
Figure 11:
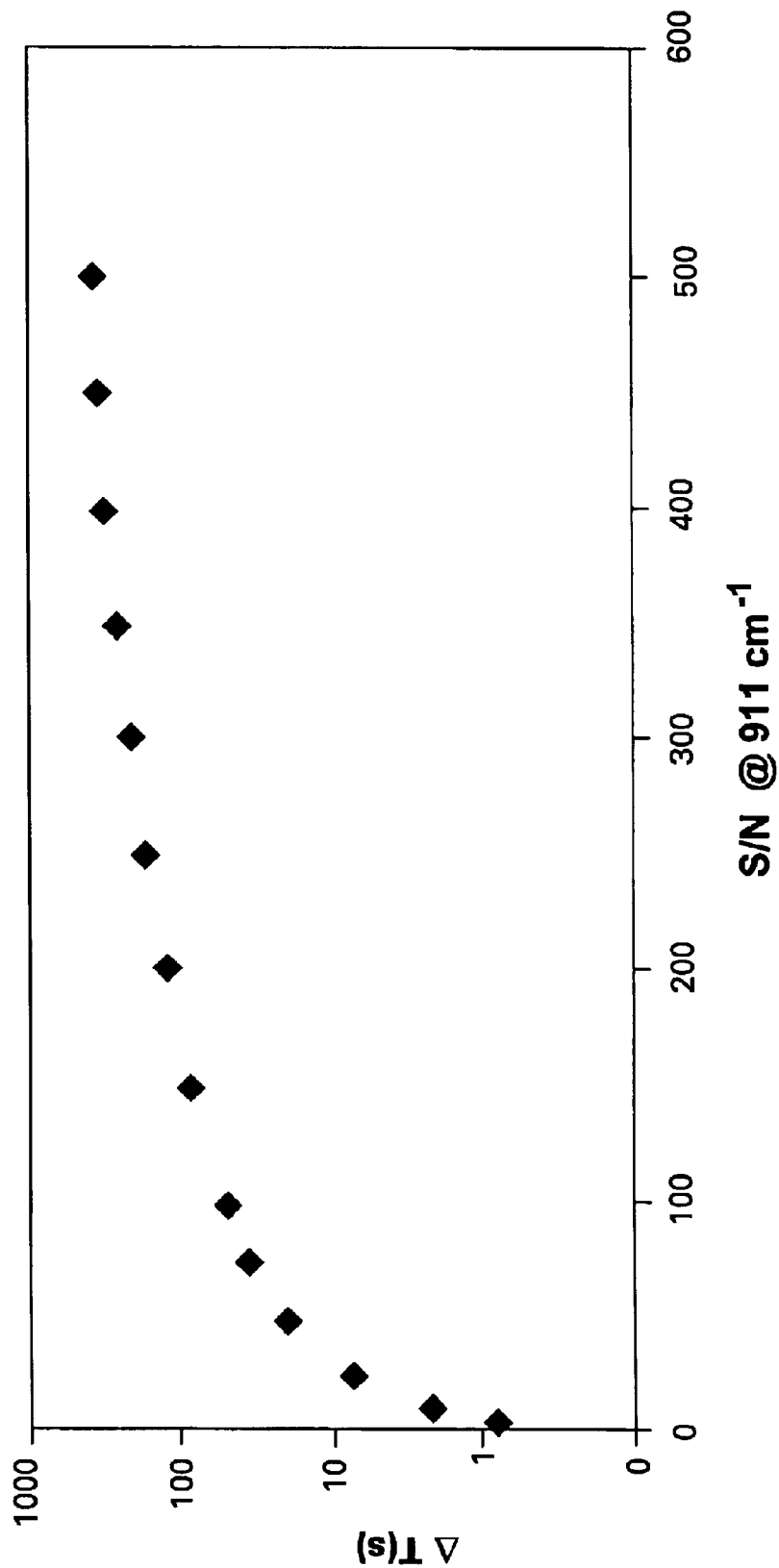
Figure 12:
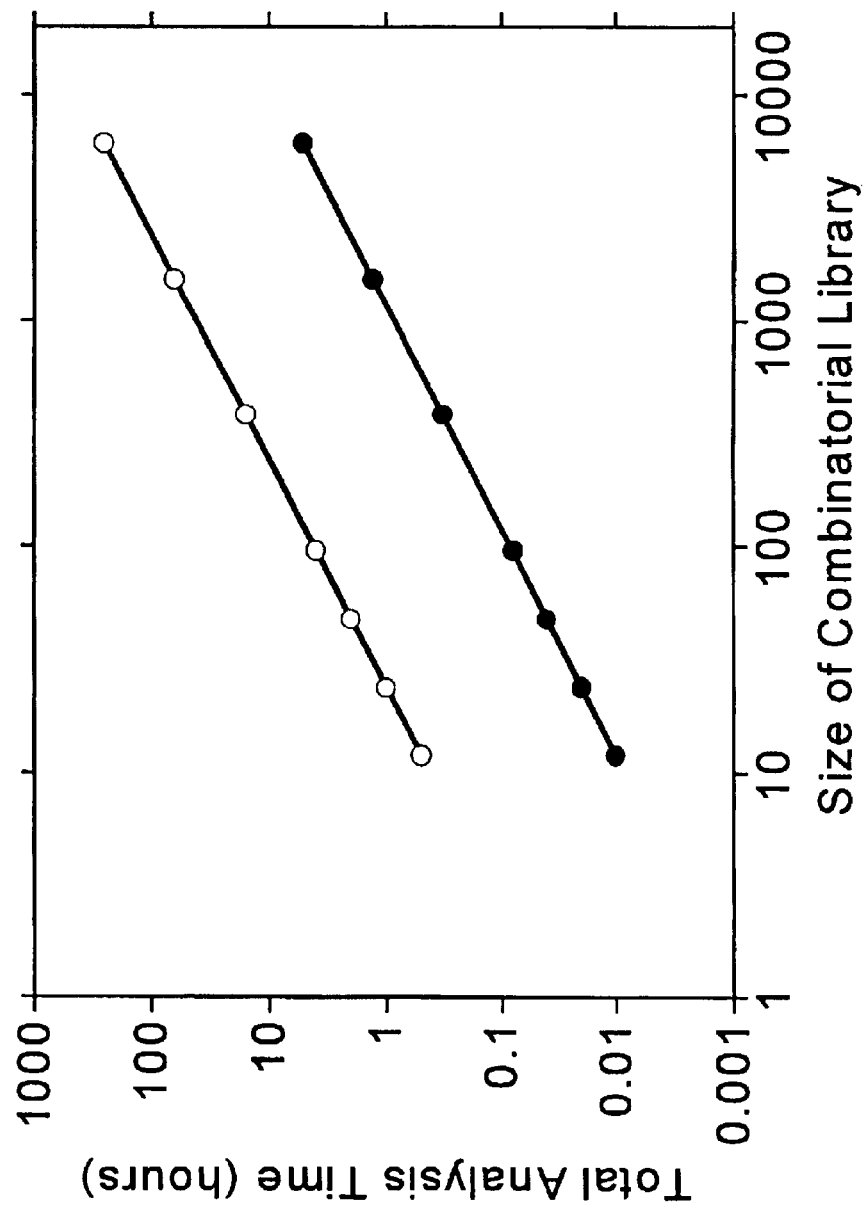

FIG. 10 illustrates an aspect of an embodiment of the invention showing the reduction of integration time $\Delta T(\Delta T=T_b-T_a)$ at a predetermined signal-to-noise ratio (S/N) in a collected signal before ($T_b$) and after ($T_a$) applying the screening rate accelerator toolbox in Raman analysis of diphenyl carbonate (DPC) at the 1072 cm$^{-1}$ band;

FIG. 11 illustrates an aspect of an embodiment of the invention showing the reduction of integration time $\Delta T(\Delta T=T_b-T_a)$ at a predetermined signal-to-noise ratio (S/N) in a collected signal before ($T_b$) and after ($T_a$) applying the screening rate accelerator toolbox in Raman analysis of diphenyl carbonate (DPC) at the 911 cm$^{-1}$ band; and FIG. 12 illustrates an aspect of an embodiment of the invention showing the improvement in screening time of combinatorial libraries of different numbers of individual samples wherein open circles comprise total analysis time for a given library of original Raman spectra before processing by the method of the invention and closed circles comprise total analysis time for a given library of spectra after signal processing by the method of the invention.

DETAILED DESCRIPTION OF THE INVENTION

The present invention provides methods and an apparatus for the rapid analysis of data from imaging, spectroscopic, scanning probe, or sensor methods by the application of mathematical transform analysis to reduce sample integration time. For example, using wavelet transform analysis, sample integration time is reduced by more than 100-fold. This reduction in integration time results in significant savings in the time required for data analysis.

In one aspect, the invention comprises a method for reducing the time required for analyzing at least one sample for a parameter of interest which comprises collecting analytical data from a sample using a predetermined integration time $T_a$ and applying mathematical transform analysis on the data, wherein the mathematical transform analysis is performed using conditions designed to achieve a predetermined signal quality response function value comprising the value obtained when samples are analyzed without mathematical transform analysis using integration time $T_b$, wherein $T_b$ is greater than $T_a$.

In an embodiment, the mathematical transform analysis comprises multivariate analysis. Preferably, the multivariate analysis comprises neural networks analysis, principal components analysis, partial least squares analysis, linear multivariate analysis, or nonlinear multivariate analysis.

In another embodiment, the mathematical transform analysis comprises discrete transform analysis. Alternatively, the mathematical transform analysis may comprise continuous transform analysis.

In yet another embodiment, the mathematical transform analysis comprises time averaging analysis, smoothing analysis or Savitsky-Golay analysis. The mathematical transform analysis may also comprise Fourier transform, Gabor transform, or Hadamard transform.

In an embodiment, the mathematical transform analysis comprises wavelet transform. In an embodiment, the wavelet transform analysis comprises a wavelet de-noising algorithm. Preferably, the wavelet de-noising algorithm comprises wavelet filters. Also preferably, the wavelet de-noising algorithm comprises a threshold/shrinkage method. Preferably, parameters of the mathematical transform are determined during the course of analysis.

Preferably, the preset signal quality response function ($y=f(x_1, x_2, x_3, \ldots x_n)$), comprises one or more measured signal parameters, (x), either used individually or combined mathematically. In an embodiment, at least one of the measured signal parameters comprises a signal-to-noise ratio. In another embodiment, at least one of the measured signal parameters comprises signal resolution. In another embodiment, at least one of the measured signal parameters comprises peak shift. In yet another embodiment, at least one of the measured signal parameters comprises signal distortion. Thus, the signal quality response function may consist of one, or a combination of signal parameters.

Where at least one of the signal parameters comprises a signal-to-noise ratio, preferably, the pre-determined signal quality response function value comprises a signal to noise ratio which ranges from 1 to 10,000. More preferably, the signal to noise ratio ranges from 2 to 5,000. Even more preferably, the signal to noise ratio ranges from 3 to 1,000.

In an embodiment, the analytical data comprises a first-order array. In an alternate embodiment, the analytical data comprises a multi-order array.

Preferably, the analytical data comprise an increase in signal resolution as a function of acquisition time. Also preferably, the analytical data comprise spectroscopic, imaging, sensor, or scanning data. More preferably, the data further comprise measurements made using Raman, luminescence, ultraviolet-visible molecular absorbance, atomic absorbance, infra-red, near infrared, surface plasmon resonance, mass spectrometry, X-ray, nuclear magnetic resonance, refractometry, interferometry, scattering, inductively coupled plasma, atomic force microscopy, scanning tunneling microscopy, microwave evanescent wave microscopy, near-field scanning optical microscopy, atomic fluorescence, laser-induced breakdown spectroscopy, Auger electron spectroscopy, X-ray photoelectron spectroscopy, ultrasonic spectroscopy, dielectric spectroscopy, microwave spectroscopy, or resonance-enhanced multiphoton ionization, and the like. Also, combinations of these techniques can be used, for example surface plasmon resonance and fluorescence, Raman and infrared, and any others. Also, different improvements and subclasses of these techniques can be used, for example, resonance Raman, surface-enhanced Raman, resonance surface-enhanced Raman, time-of-flight mass spectrometry, secondary ion mass spectrometry, ion mobility spectrometry, and the like. The techniques used to collect the analytical data may also comprise photon probe microscopy, electron probe microscopy, ion probe microscopy, field probe microscopy, scanning probe microscopy, and the like. In an embodiment, analytical data is provided using techniques relying on collection of electromagnetic radiation in the range from 0.05 Angstroms to 500 millimeters (mm).

The sample may be inorganic material, organic material, polymeric material, biological material, or combinations thereof. In an embodiment, the sample comprises polycarbonate. Further, the concentration ranges of species of interest analyzed using these techniques can range from detected single molecules to concentrations of up to 100 percent of materials of interest. Thus, in an embodiment, the sample may comprise a single molecule. In another embodiment, the parameter of interest may comprise up to 100% of the sample. Any type of single molecule spectroscopy and imaging can utilize the method of this invention.

In an embodiment, the invention comprises computer readable media comprising software code for performing the methods of the invention. The present invention also comprises systems using the methods of the invention.

In another aspect, the invention comprises a method for reducing the time required for analyzing at least one sample for a parameter of interest which comprises: selecting a pre-determined signal quality response function; selecting a pre-determined integration time $T_a$; collecting analytical data from the sample with integration time $T_a$; applying a screening rate accelerator toolbox comprising mathematical transform analysis to the data, wherein the mathematical transform analysis is performed using conditions designed to achieve a pre-determined signal quality response function value comprising the value obtained when samples are analyzed without mathematical transform analysis using integration time $T_b$, wherein $T_b$ is greater than $T_a$; and analyzing the data processed by the screening rate accelerator toolbox for the parameter of interest.

In an embodiment, the mathematical transform analysis comprises multivariate analysis. Preferably, the multivariate analysis comprises neural networks analysis, principal components analysis, partial least squares analysis, linear multivariate analysis, or nonlinear multivariate analysis.

In another embodiment, the mathematical transform analysis comprises discrete transform analysis. Alternatively, the mathematical transform analysis may comprise continuous transform analysis.

In yet another embodiment, the mathematical transform analysis comprises time averaging analysis, smoothing analysis or Savitsky-Golay analysis. The mathematical transform analysis may also comprise Fourier transform, Gabor transform, or Hadamard transform.

In an embodiment, the mathematical transform analysis comprises wavelet transform. In an embodiment, the wavelet transform analysis comprises a wavelet de-noising algorithm. Preferably, the wavelet de-noising algorithm comprises wavelet filters. Also preferably, the wavelet de-noising algorithm comprises a threshold/shrinkage method. Preferably, parameters of the mathematical transform are determined during the course of analysis.

The method allows for flexibility in the decision as to whether the screening rate accelerator toolbox is required. In an embodiment, the method comprises the steps of determining whether the analytical data collected from the sample with integration time $T_a$ satisfies the pre-determined signal quality response function value prior to applying the screening rate accelerator toolbox and applying the screening rate accelerator toolbox if the collected data does not satisfy the pre-determined signal quality response function value, but not if the collected data does satisfy the pre-determined signal quality response function value.

The method also permits iterative application of the screening rate accelerator toolbox. Thus, in an embodiment, the method includes the steps of: determining whether the data processed by the screening rate accelerator toolbox satisfies the pre-determined signal quality response function value; and if the processed data does not satisfy the pre-determined signal quality response value, re-applying the screening rate accelerator toolbox using a mathematical transform analysis different from the analysis previously applied until the data processed using the screen rate accelerator toolbox either satisfies the pre-determined signal quality response function value or comprises an optimized signal quality response function value.

In some cases, even with application of the screening rate accelerator toolbox, the data collected with an integration time $T_a$ may not satisfy the signal quality response function value. Thus, in an embodiment, the method includes the steps of repeating the method with a new, larger value for $T_a$ if the data which is optimized using the screening rate accelerator toolbox does not satisfy the pre-determined signal quality response function value.

One purpose of the method is to minimize the time required for processing large arrays of experimental samples. Thus, in an embodiment, if the collected analytical data does not require application of the screening rate accelerator toolbox to satisfy a pre-determined signal quality response function value, a shorter pre-determined integration time $T_a$ is selected, and the method performed using the new value for $T_a$. By reducing $T_a$ to a value which allows for the pre-determined signal quality response function value (e.g. S/N=20) to be obtained upon application of the screening rate accelerator toolbox, the overall time required for sample analysis is minimized.

Preferably, the preset signal quality response function comprises one or more measured signal parameters, either used individually or combined mathematically. In an embodiment, at least one of the measured signal parameters comprises a signal-to-noise ratio. Preferably, the signal quality response function value comprises a signal to noise ratio of 1 to about 10,000. More preferably, the signal quality response function value comprises a signal to noise ratio of 2 to 5,000. Even more preferably, the signal quality response function value comprises a signal to noise ratio of 3 to 1,000.

In another embodiment, at least one of the measured signal parameters comprises signal resolution. In another embodiment, at least one of measured the signal parameters comprises peak shift. In yet another embodiment, at least one of the signal parameters comprises signal distortion.

In an embodiment, the relative improvement in signal integration time ($T_b/T_a$) ranges from about 1.5 to 1,000 fold. In another embodiment, the relative improvement in signal integration time ($T_b/T_a$) ranges from about 1.5 to 500 fold. In yet another embodiment, the relative improvement in signal integration time ($T_b/T_a$) ranges from about 1.5 to 200 fold.

In an embodiment, the analytical data comprises a first-order array. In an alternate embodiment, the analytical data comprises a second-order or higher array such as multi-order arrays and the like.

In an embodiment, evaluation of each individual sample in an array of samples is substantially simultaneous. In an alternate embodiment, each individual sample in an array of samples is evaluated separately.

Preferably, the analytical data comprise an increase in signal resolution as a function of acquisition time. Also preferably, the analytical data comprise spectroscopic, imaging, sensor, or scanning data. More preferably, the data further comprise measurements made using Raman, luminescence, ultraviolet-visible molecular absorbance, atomic absorbance, infra-red, near infrared, surface plasmon resonance, mass spectrometry, X-ray, nuclear magnetic resonance, refractometry, interferometry, scattering, inductively coupled plasma, atomic force microscopy, scanning tunneling microscopy, microwave evanescent wave microscopy, near-field scanning optical microscopy, atomic fluorescence, laser-induced breakdown spectroscopy, Auger electron spectroscopy, X-ray photoelectron spectroscopy, ultrasonic spectroscopy, dielectric spectroscopy, microwave spectroscopy, resonance-enhanced multiphoton ionization, and the like. Also, combinations, improvements, and sub-classes of these techniques can be used, for example surface plasmon resonance and fluorescence, Raman and infrared, and any others. The techniques used to collect the analytical data may also comprise photon probe microscopy, electron probe microscopy, ion probe microscopy, field probe microscopy, scanning probe microscopy, and the like. In an embodiment, analytical data is provided using techniques relying on collection of electromagnetic radiation in the range from 0.05 Angstroms to 500 millimeters (mm).

The sample may be inorganic material, organic material, polymeric material, biological material, or combinations thereof. In an embodiment the sample comprises polycarbonate. Further, concentration ranges of species of interest analyzed using these techniques can range from detected single molecules to concentrations of up to 100 percent of materials of interest. Any type of single molecule spectroscopy and imaging can utilize the method of this invention.

In an embodiment, the invention comprises computer readable media comprising software code for performing the methods of the invention. The present invention also includes systems comprising the method of the invention.

In another aspect, the present invention comprises an apparatus for analyzing at least one sample for a parameter of interest using a pre-determined signal quality response function which comprises: a collecting system for collecting analytical data comprising the parameter of interest from a sample; a processing system for processing the analytical data; a screening rate accelerator toolbox for applying mathematical transform analysis to the data; a data analysis system for determining whether the data processed by the screening rate accelerator toolbox satisfies a pre-determined signal quality response function value; and a statistical toolbox for analyzing the processed data for the parameter of interest.

In an embodiment, the mathematical transform analysis comprises multivariate analysis. Preferably, the multivariate analysis comprises neural networks analysis, principal components analysis, partial least squares analysis, linear multivariate analysis, or nonlinear multivariate analysis.

In another embodiment, the mathematical transform analysis comprises discrete transform analysis. Alternatively, the mathematical transform analysis may comprise continuous transform analysis.

In yet another embodiment, the mathematical transform analysis comprises time averaging analysis, smoothing analysis or Savitsky-Golay analysis. The mathematical transform analysis may also comprise Fourier transform, Gabor transform, or Hadamard transform.

In an embodiment, the mathematical transform analysis comprises wavelet transform. Preferably, the parameters of the mathematical transform are determined during the course of analysis.

In an embodiment, the pre-determined signal quality response function comprises one or more measured signal parameters. In an embodiment, at least one of the measured signal parameters comprises a signal-to-noise ratio. In another embodiment, at least one of the measured signal parameters comprises signal resolution. In another embodiment, at least one of the measured signal parameters comprises peak shift. In yet another embodiment, at least one of the measured signal parameters comprises signal distortion.

In an embodiment, the apparatus of the invention includes at least one energy source for interacting with a sample. Preferably, the energy source is a light source, an ion source, or a radiation source. In an embodiment, the apparatus does not contain a light source. The data collection system may be an optical spectrometer, an ion spectrometer, a mass detector, an imaging camera, or other instrument capable of quantifying spectral or imaging information.

In an embodiment, the analytical data comprises a first-order array. In an alternate embodiment, the analytical data comprises a multi-order array.

In an embodiment, evaluation of each individual sample in an array of samples is substantially simultaneous. In an alternate embodiment, each individual sample in an array of samples is evaluated separately.

Preferably, the analytical data comprise an increase in signal resolution as a function of acquisition time. Also preferably, the analytical data comprise spectroscopic, imaging, sensor, or scanning data. More preferably, the data further comprise measurements made using Raman, luminescence, ultraviolet-visible molecular absorbance, atomic absorbance, infra-red, near infrared, surface plasmon resonance, mass spectrometry, X-ray, nuclear magnetic resonance, refractometry, interferometry, scattering, inductively coupled plasma, atomic force microscopy, scanning tunneling microscopy, microwave evanescent wave microscopy, near-field scanning optical microscopy, atomic fluorescence, laser-induced breakdown spectroscopy, Auger electron spectroscopy, X-ray photoelectron spectroscopy, ultrasonic spectroscopy, dielectric spectroscopy, microwave spectroscopy, resonance-enhanced multiphoton ionization, and the like. Combinations, improvements, and subclasses of these techniques can also be used. The techniques used to collect analytical data may also comprise photon probe microscopy, electron probe microscopy, ion probe microscopy, field probe microscopy, scanning probe microscopy, and the like. In an embodiment, analytical data is provided using techniques relying on collection of electromagnetic radiation in the range from 0.05 Angstroms to 500 millimeters (mm). For example, detection of thermal or luminescence emission is performed using spectroscopy or imaging. In yet another embodiment, the apparatus comprises computer readable media comprising software code.

The methods and apparatus described herein provide a means to reduce sample integration time for spectroscopic data, imaging arrays, sensor array data and the like. As used herein, integration time is defined as the time during which a detector acquires incoming photons, and data acquisition time is defined as the total time required to collect, process, and store individual signals from an analyzed sample or its certain portion.

The method of the present invention may be used to analyze a parameter of interest in a sample, wherein a parameter of interest comprises a chemical, physical, or mechanical aspect of the sample which can be monitored experimentally. Parameters of interest include, but are not limited to, starting reaction components, chemical intermediates, reaction by-products, final products, and mechanical parameters such as moduli, and the like. For example, in the synthesis of melt polycarbonate, a parameter of interest may be the starting components bisphenol A or diphenyl carbonate, oligomer intermediates, phenol, Fries products, or the final polymer.

As described herein, the sample may comprise individual samples, multiple individual samples arranged in a fixed format (i.e. multi-element arrays), as well as a plurality of individual samples. Multi-element arrays may be arranged in a geometrically defined array. Thus, in an embodiment, a sample comprises a combinatorial library. In an embodiment, individual regions in the sample array or library are evaluated separately. In an alternate embodiment, evaluation of the entire array or library is substantially simultaneous.

The methods and devices of the present invention apply mathematical transform analysis to reduce the integration time required to measure a parameter of interest in a sample. Any method of mathematical transform analysis which results in a decrease in sample integration time as a result of the mathematical transformation of the data may be used. Thus, in an embodiment, the mathematical transform analysis comprises multivariate analysis using multivariate measurement, wherein multivariate measurement comprises measurements of more than one variable or response for each sample, and multivariate analysis is a mathematical analysis in which more than one variable or response is analyzed for each sample (Beebe, K. R., et al., In Chemometrics: A Practical Guide, p. 6, Wiley, New York, N.Y., 1998). For example, a whole or a portion of a collected optical spectrum comprising multiple wavelengths may be analyzed for a single analyte (Beebe, K. R., et al., at 6).

Types of multivariate analysis include linear multivariate analysis, nonlinear multivariate analysis, partial least squares analysis, principal components analysis, and neural networks analysis. Generally, linear multivariate analysis is used to describe linear relationships between independent and dependent variables using straight line calibration functions, and non-linear multivariate analysis is used to describe nonlinear relationships between independent and dependent variables (Otto, M., In Chemometrics: Statistics and Computer Application in Analytical Chemistry, p. 215, Wiley-VCH, Weinheim, Germany, 1999). Principal components analysis and factor analysis are transforms that find and interpret hidden complex and possibly causally determined relationships between features in a data set; the correlating features are then converted to factors which are themselves non-correlated (Einax, J. W., et al., In Chemometrics in Environmental Analysis, p. 164, VCH, Weinheim, 1997). Partial least squares (PLS) analysis and principal components regression (PCR) analysis make use of an inverse calibration approach where it is possible to calibrate for the desired component(s) while implicitly modeling the other sources of variation; the difference between PLS and PCR is in how the factors are calculated (Beebe, K. R., et al., Chemometrics: A Practical Guide, p. 279, Wiley, New York, N.Y., 1998). Neural networks analysis describes analysis of a data set to a specific problem by iterative adjustment of weights in a net during the learning process; this adaptation may be done either by comparison of the desired result with the data at the output of the net (supervised learning) or by maximizing differences in the learning data based on an arbitrary criterion of similarity (unsupervised learning) (Hierlemann, A., et al., In Sensors Update, Vol. 2, pp. 119–180, Eds. H. Baltes, W. Göpel, and J. Hesse, VCH, Weinheim, 1996).

The mathematical transform analysis may comprise continuous transform analysis or discrete transform analysis. Continuous transform analysis comprises the analysis of continuous signals, such as for example, analogue voltage, which is defined for all values of time (C. L. Phillips and J. M. Parr, In Signals, Systems, and Transforms, p. 2, Prentice Hall, Upper Saddle River, N.J., 1999). An example of continuous transform is integration (C. L. Phillips and J. M. Parr, at 390). Discrete transform analysis comprises the analysis of discrete signals such as the intensity of light reaching each pixel of a diode array detector (C. L. Phillips and J. M. Parr, at 2). An example of discrete transform is summation (C. L. Phillips and J. M. Parr, at 390).

The method of mathematical transform may also comprise time averaging analysis where measurements are repeated and the corresponding data added (Vandeginste, B. G. M., et al., Handbook of Chemometrics and Qualimetrics, Part B, p. 538–539, Elsevier, Amsterdam, The Netherlands, 1998) or smoothing analysis which uses an accumulation of values of a number of data points in a small segment or window in the same scan. The smoothing function may be a block function, a polynomial function or an exponential function (Vandeginste, B. G. M., et al., at 535–553). Alternatively, the method of mathematical transform may also comprise Savitsky-Golay analysis which is a combination of smoothing and derivative analysis (Vandeginste, B. G. M., et al., at 550).

The method of mathematical transform may also comprise Fourier transform, Gabor transform, or Hadamard transform. Fourier transform comprises a method of representing mathematical models of signals and systems in the frequency domain using sine and cosine functions (C. L. Phillips and J. M. Parr, In Signals, Systems, and Transforms, p. 174, Prentice Hall, Upper Saddle River, N.J., 1999), Gabor transform comprises a short-time Fourier transform employing Gaussian weight functions (T. Masters, Signal and Image Processing With Neural Networks: A C++ Sourcebook, p. 150, Wiley, New York, N.Y., 1994), and Hadamard comprises encoding signals using periodic square wave functions (P. J. Treado and M. D. Morris, Analytical Chemistry 61: 723A–734A (1989).

The method of mathematical transform may also comprise wavelet transform. As used herein, the term wavelet transform analysis comprises the use of an inverse transform matrix which applies an infinite set of possible basis functions comprising wavelets, mother wavelets, analyzing wavelets and the like, and wherein the window within the time-frequency plane is allowed to vary.

The wavelet transform analysis may comprise a wavelet de-noising algorithm, where a wavelet de-noising algorithm is a mathematically defined combination of wavelet transforms which are designed specifically to de-noise spectra. In an embodiment, the adaptive wavelet de-noising algorithm tries many different combinations of wavelet filters and threshold/shrinkage options to maximize the signal quality response function (e.g. signal-to-noise ratio) for that spectrum. After shrinkage, an inverse transform is computed to produce a wavelet processed signal.

Like Fourier transforms, wavelet transforms comprise an inverse transform matrix that can be viewed as a rotation in function space. These transforms provide a means of mapping signals from one domain to another, such as from the time-scale domain to the frequency domain. Unlike Fourier transform analysis, which is limited to transformation functions utilizing only sines and cosines, wavelet transforms utilize an infinite set of possible basis functions, and allow for the window within the time-frequency plane to vary. The flexibility inherent to wavelet analysis allows analysis of both short basis, high-frequency functions (to isolate signal discontinuities) as well as long basis, low-frequency functions (to obtain detailed frequency analysis) (see e.g., Amara, IEEE Computational Sciences and Engineering, 2:50–61 (1995)).

Wavelet analysis has been applied for processing signals for a variety of applications including the analysis of spectra. For example wavelet analysis has been used to determine relative ion abundances in mass spectrometry (U.S. Pat. No. 5,436,447), to provide classification of sensor data (U.S. Pat. No. 5,561,431), to evaluate peak intensities in flow-injection analysis (Bos, M. et al., Anal. Chim. Acta, 267:73–80 (1992)), to extract the relevant components from spectral data for multivariate calibration (Jouan-Rimbaud, D., et al., Anal. Chem., 69:4317–4323 (1997)), for pattern recognition (Walczak, B., et al., Anal. Chem., 68:1742–1747 (1996)), and for classification of spectra (Bos, M., et al., Chemom. Intell. Lab. Syst., 23:115–122 (1994)). Wavelets have been used to compress spectra (Bos, M. et al., Chemom. Intell. Lab. Syst., 23:115–122 (1994); Chau, F. T. et al., Appl. Spectrosc., 50:339–348 (1996)), to standardize spectra (Walczak, B., et al., Chemom. Intell. Lab. Syst., 36:41–51 (1997)), and to characterize non-parameterized magnetic resonance (Young, K., et al., Magn. Reson. Med., 40:816–821 (1998)) and oscillographic signals (Zheng, J., et al., Analyst, 124:893–896 (1999)).

Wavelets are often used to reduce noise via wavelet shrinkage and thresholding techniques (see e.g. Donoho, D., Different Perspectives on Wavelets, Proceeding of Symposia in Applied Mathematics, 47:173–205 (1993)). Wavelets have been used to remove noise from synthetic Gaussian peaks (Mittermayr, C. R. et al., Chemom. Intell. Lab. Syst., 34:187–202 (1996)), near-IR (Walczak, B., et al., Chemom. Intell. Lab. Syst., 36:81–94 (1997)) and NMR spectra (Walczak, B. et al., Trends Anal. Chem., 16:451–463 (1997)), and images such as SIMS (Nikolov, S. G., et al., Chemom. Intell. Lab. Syst., 34:263–273 (1996)) and ultrasound (U.S. Pat. Nos. 5,619,998; 5,497,777; and Alsberg, B. K. et al., Chemom. Intell. Lab. Syst., 37:215–239 (1997)).

Wavelet filters are a means to apply pre-determined wavelet functions. The wavelet used may include wavelets of the Daubechies family, the Symmlet family, the Haar family, the Coiflet family, the Beylkin family, and the like. Within each family are wavelet subclasses distinguished by the number of coefficients and the level of iteration employed. Wavelets may also be classified in a family by the number of vanishing moments, where vanishing moments comprise a set of mathematical relationships directly related to the number of wavelet coefficients. For example, Daubechies asymmetrical filters are minimal phase filters that generate wavelets that have minimal support for a given number of vanishing moments. Symmlets are also wavelets with a minimum size support for a given number of vanishing moments, but are generally symmetrical. Both filters are defined by the number of vanishing moments, which differ depending on the shape and size of the analyte signal.

The de-noising algorithm may also include a thresholding procedure. A threshholding procedure, such as soft thresholding or wavelet shrinking, comprises a mathematical transformation whereby wavelet coefficients caused by noise can be reduced. Thus, threshholding may be applied to the wavelet coefficients to shrink or remove those wavelet coefficients mainly due to noise components. Two key parameters for the shrinkage step are the shrinkage method and the low frequency cutoff. These parameters are preferably optimized for each spectrum using shrinkage methods including, but not limited to, Visu, SURE, and MAD, which are known to those of skill in the art (see e.g. D. L. Donoho and I. M. Johnstone, WAVELAB™ toolbox available throught the Stanford University deparment of Statistics website.

The method comprises applying mathematical transform analysis to achieve a preset, or pre-determined, signal quality response function value. The pre-determined signal quality response function, $y=f(x)$, by which the processed spectra are evaluated may vary depending on the nature of the experiment. The inputs to the signal quality response function $(y=f(x))$ may consist of one or more signal parameters either used individually or combined together mathematically.

For example, the pre-determined spectral parameter (x) may comprise the signal-to-noise ratio (S/N) at specific peaks in the spectra. As defined herein, signal-to-noise ratio is defined as the amplitude of the measured response for a component of interest in the sample as compared to the root-mean square of the measured response due to general background.

In another embodiment, the signal quality parameter of interest comprises peak shift in a specific region of the spectra, where peak shift comprises a change in the position (as opposed to the amplitude) of a measured signal. For example, spectroscopic peaks which correspond to known starting materials may shift due to chemical reaction or exposure to a specific environment.

In yet another embodiment, the signal quality parameter comprises band distortion, where band distortion comprises a change in the shape of a measured signal. For example, spectroscopic peaks which correspond to known reaction materials may be distorted due to physical force/stress applied to the sample, or chemical/electronic interaction with the surrounding environment. Also, un-optimized wavelet de-noising parameters such as the number of vanishing moments or the threshold/shrinkage method may also cause band distortion. Methods of quantifying band distortion include calculating of peak area, as for example, using integration techniques such as, but not limited to, the extended trapezoidal rule. Alternatively band distortion may be quantified by measuring peak (band) width at either the base or half-height, using methods known to those in the art.

In another embodiment, the signal quality parameter comprises band or peak resolution. As defined herein, band resolution is a measure of how completely two neighboring peaks or bands are separated from each other, wherein increasing resolution comprises increasing band separation, and a resolution of zero indicates two neighboring peaks are completely overlapped with each other. For example, resolution may be calculated as $R_s=2*[(R1-R2)/(W1+W2)]$ for Gaussian-shaped peaks, where R1 and R2 are the locations of the neighboring peaks, and W1 and W2 are the widths at half-height for the neighboring peaks, or other methods standard in the art (D. A. Skoog and G. G. Leary, Principals of Instrumental Analysis, $4^{th}$ Ed., Saunders College Publishing, Fort Worth, Tex., 1992, p. 592).

The method may be used to analyze data presented as first-order or higher order arrays. A first order array comprises a one dimensional data set, such as, but not limited to, spectra, chromatograms, ionograms, sensor array data, and the like. A second-order array comprises data sets which are two-dimensional, such as images of combinatorial libraries, gas chromatograph-mass spectroscopy data (GC/MS), excitation-emission fluorescence maps, time dependent monitoring of processes, and the like.

The present invention also includes systems comprising the method of the invention. The system can be a stand-alone system that performs the analysis of samples directly, or it can be incorporated in a more general system that also includes a separation step, followed by a detection step. The separation can be performed using any system that analyzes relatively large amounts of materials or a system that analyzes very small amounts of materials (nanogram, femtogram, and less). An example of the latter system can be a lab-on-a-chip system. As another example, a system may comprise a sensor element followed by a detection step. As described herein, sensors generally include a material that changes its spectroscopic or other property as a function of analyte concentration in proximity to this element.

The invention also includes an apparatus for analyzing at least one sample for a parameter of interest using a predetermined signal quality response function which comprises: (a) a collecting system for collecting analytical data comprising a parameter of interest from a sample; (b) a processing system for processing the data; (c) a screening rate accelerator toolbox for applying wavelet transform analysis to the data; (d) a data analysis system for determining whether the wavelet processed data satisfies a pre-determined signal quality response function value; and (e) a statistical toolbox for analyzing the processed data for the parameter of interest.

As used herein, a collecting system is defined as a set of hardware and software components to collect spectroscopic or imaging signals. The hardware components can include any components needed to generate and record the signals from the sample region of interest. A processing system is defined as a set of hardware and software components to process the collected analytical data into a form acceptable for further analysis, and a screening rate accelerator toolbox is essentially a collection of mathematical functions used to apply mathematical transform analysis to the data in an interactive or iterative manner. As used herein, a data analysis system is defined as a system that compares measured data from a sample (e.g. the signal quality response function value) to a pre-determined standard (e.g. a pre-determined signal quality response function value). The measured data may be processed by the screening rate accelerator toolbox or unprocessed. Finally, a statistical toolbox is essentially a collection of mathematical functions that can be used analyze data (wavelet processed or unprocessed) for a parameter of interest.

The samples may be analyzed using sensor array techniques. As used herein, a sensor array is a set of sensor elements combined with a single or multiple detectors. Each sensor element can include a material that changes its spectroscopic or other property as a function of analyte concentration in proximity to the element. Using sensor array techniques, a spectroscopically inactive (undetectable) analyte can be detected with a spectroscopic or imaging system that utilizes the method of the invention.

In an embodiment, the apparatus of the invention includes no light source for exciting a sample. In this case, detection of thermal or luminescence emission is performed using spectroscopy or imaging. Luminescence emission can include chemoluminescence, bioluminescence, triboluminescence, electroluminescence, and any other type of radiation emission generated by a process that does not involve an absorption of incoming photons and a process that does include absorption of incoming photons.

In an embodiment, the invention describes the use of mathematical transform analysis to reduce the data acquisition time for spectroscopic analysis of sample arrays. The present invention is particularly useful for the analysis of signal from each element of a multi-element sample system such as a combinatorial library and the like. One benefit of the screening rate accelerator toolbox of the present invention can be expressed as the reduction of integration time $\Delta T$ needed to achieve a predetermined signal response function, such as a defined signal-to-noise ratio (S/N), in a collected signal before, $T_b$, and after, $T_a$, applying the screening rate accelerator toolbox:

$$\Delta T = T_b - T_a$$

Increases in screening throughput can potentially be achieved by using certain hardware capabilities. For example, an increase in the power of a light source in optical spectroscopic applications can be used for the reduction of integration time of spectral and/or image acquisition. However, an increase in excitation power often causes premature photo-bleaching and other types of sample degradation. Another potential approach for decreasing integration time is by reduction in the noise level of a photodetector. In most systems, however, such noise reduction requires significant cooling of the detector, which adds to the size, cost, and complexity of the system.

In an embodiment, the invention uses a screening rate accelerator toolbox comprising wavelet transform to reduce data acquisition time. For example, the reduction in data acquisition time can be accomplished by applying wavelet algorithms to de-noise data sets. The de-noised data allows for a preset signal quality response function (e.g. S/N=20) to be obtained with a reduced sample integration time, which thereby reduces the time required for data acquisition for each sample. In an embodiment, the data sets are one-dimensional, such as spectra, chromatograms, ionograms, sensor array data and the like. In another embodiment, the data sets are two-dimensional, such as images of combinatorial libraries, gas chromatograph-mass spectroscopy data (GC/MS), excitation-emission fluorescence maps, time-dependent monitoring of processes, and the like. Preferably, reduction in signal integration results in a significant acceleration in the screening process.

Figure 1:
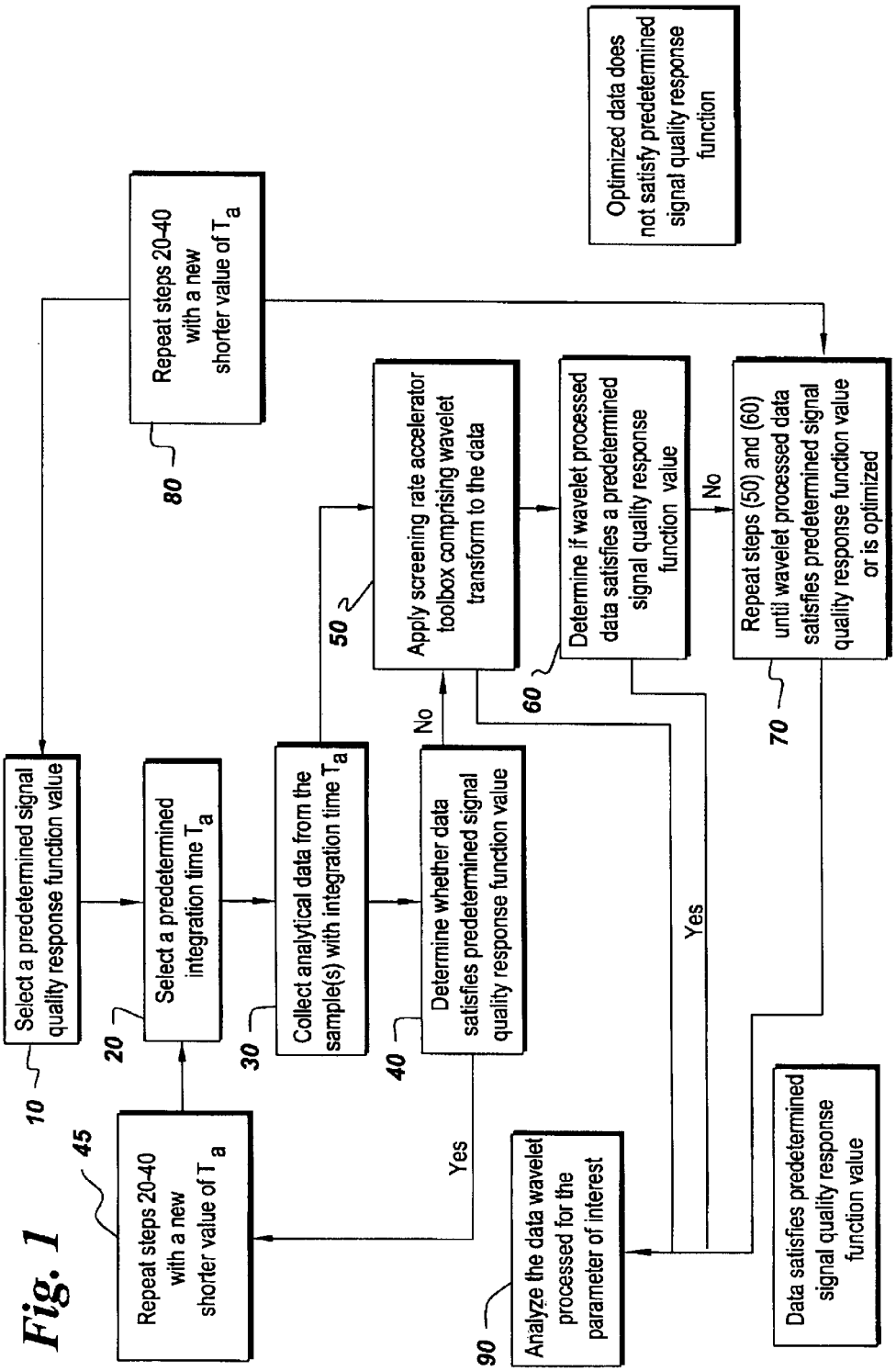
FIG. 1 is a flow chart illustrating an embodiment of the overall method of the present invention.

Referring now to FIG. 1, in one aspect, the invention comprises a method for reducing the time required for analyzing a sample for a parameter of interest which comprises: (10) selecting a pre-determined signal quality response function; (20) selecting a pre-determined integration time $T_a$; (30) collecting analytical data from the sample with integration time $T_a$; (50) applying a screening rate accelerator toolbox comprising mathematical transform analysis to the data, wherein the mathematical transform analysis is performed using conditions designed to achieve a pre-determined signal quality response function value comprising the value obtained when samples are analyzed without mathematical transform analysis using integration time $T_b$, wherein $T_b$ is greater than $T_a$; and (90) analyzing the data processed by the screening rate accelerator toolbox for the parameter of interest. In an embodiment, the method also comprises (40) determining whether the analytical data collected from the sample with integration time $T_a$ satisfies the pre-determined signal quality response function value prior to applying the screening rate accelerator toolbox and applying the screening rate accelerator toolbox if the collected data does not satisfy the pre-determined signal quality response function value, but not if the collected data does satisfy the pre-determined signal quality response function value. Also, in an embodiment, if the collected analytical data does not require application of the screening rate accelerator toolbox to satisfy a pre-determined signal quality response function value, a shorter pre-determined integration time $T_a$ is selected, and the method performed using the new value for $T_a$ (45).

The method permits iterative application of the screening rate accelerator toolbox. Thus, in an embodiment, the method includes (60) determining whether the data processed by the screening rate accelerator toolbox satisfies the pre-determined signal quality response function value; and if the processed data does not satisfy the pre-determined signal quality response value, (70) re-applying the screening rate accelerator toolbox using a mathematical transform analysis different from the analysis previously applied until the data processed using the screen rate accelerator toolbox either satisfies the pre-determined signal quality response function value or comprises an optimized signal quality response function value.

In some cases, even with application of the screening rate accelerator toolbox, the data collected with an integration time $T_a$ may not satisfy the signal quality response function value. Thus, in an embodiment, the method includes (80) repeating the method with a new, larger value for $T_a$ if the data which is optimized using the screening rate accelerator toolbox does not satisfy the pre-determined signal quality response function value.

Figure 2:
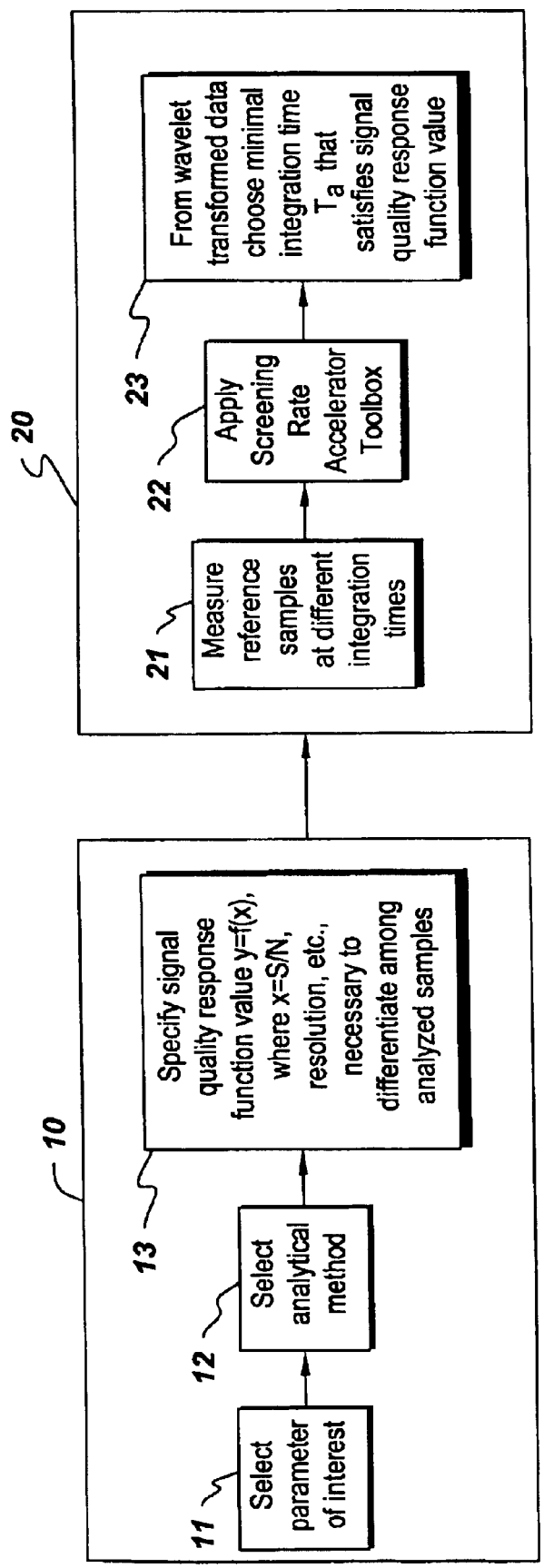
FIG. 2 illustrates an aspect of an embodiment of the method of the invention detailing steps for determination of the minimal integration time that satisfies a signal quality response function.

Generally, the method requires selection of a parameter of interest and an evaluation of the limits of the data resolution for the parameter of interest. Referring now to FIG. 2, in the high throughput screening (HTS) method of the invention, a parameter of interest, such as a specific spectral peak which corresponds to a distinct chemical component (e.g. diphenyl carbonate), or sample parameter (e.g. molecular weight) is chosen (11) to be measured using a preferred analytical method (12). The analytical method may comprise spectral or imaging techniques known to those in the art, such as Raman spectroscopy, fluorescence spectroscopy, absorbance spectroscopy, and the like. A specific signal quality response function (e.g., the signal-to-noise ratio, S/N, for a specific spectral region) is then chosen (13). Alternatively, the inputs to the signal quality response function may consist of multiple signal parameters (e.g. S/N and peak resolution) combined together mathematically ($y=f(x_1, x_2, \ldots x_n)$). For example, a multi-criteria signal quality response function can be evaluated by summation of individual signal quality parameters multiplied by weighting factors ($y=w_1*x_1 + w_2*x_2 + \ldots w_n*x_n$), where $w_1, w_2 \ldots w_n$ are specific weighting factors, and $x_1, x_2 \ldots x_n$ are the outputs of individual signal quality parameters. It will be recognized that other common mathematical manipulations such as logarithms, exponentials, cross-products, and the like, can be used to combine the individual signal quality parameters together mathematically to form a signal quality response function.

Using reference data measured for controls comprising preset values for the parameter of interest (21), the screening rate accelerator toolbox of the present invention is applied to the data (22) and a minimum integration time, ($T_a$), which satisfies the preset signal quality response function value (y) is chosen (23). For example, reference spectra or data may be used to select baseline values comprising an absence of analyte, and thereby define noise (N), and to find spectral regions which are specific to the reaction components of interest, and thereby define signal (S). An integration time which allows for a pre-determined signal-to-noise ratio (e.g. of 20, or any other pre-determined value) at a specific peak or set of peaks is then determined using the reference data. This integration time is then used for the subsequent screening of samples comprising unknown amounts of the parameter(s) of interest.

Figure 3:
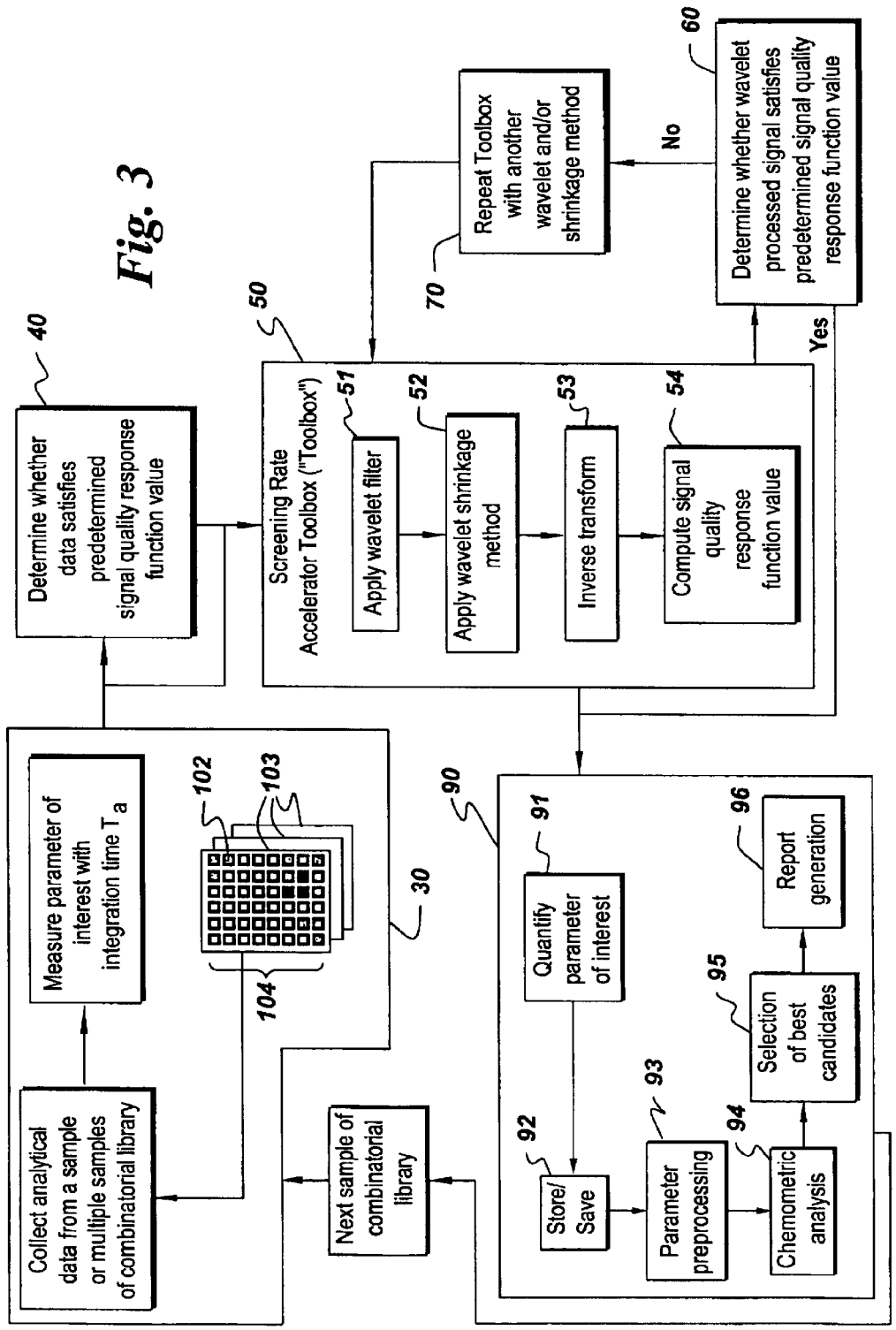
FIG. 3 illustrates an aspect of an embodiment of the method of the invention detailing the application of the screening rate accelerator toolbox in serial or parallel screening of an array of samples.

FIG. 3 depicts the method of the present invention using wavelet transform as the mathematical transform of the screening rate accelerator toolbox for the analysis of experimental sample 102 which is one of several elements arranged in sample array 104. For example, a typical sample array comprises a 384-well microtiter plate reactor, or similar array. The parameter of interest is measured (30), using the appropriate predetermined spectral or imaging technique (e.g. Raman spectroscopy). The data may then be evaluated (40) to determine whether it satisfies a pre-determined signal quality response function value or whether to apply the screening rate accelerator toolbox of the invention (50). Alternatively, the data may automatically be processed by the screening rate accelerator toolbox without pre-analysis step (40). The screening rate accelerator toolbox allows for iterative application of wavelet transforming algorithms to the dataset of interest to transform the data and thereby reduce sample integration time and provide an accelerated screening rate. In an embodiment, the algorithm de-noises the data. Preferably, the algorithm comprises wavelet filters (51). Also preferably, the algorithm comprises threshold/shrinkage parameters (52). In an embodiment, the parameters of the wavelet transformation algorithm are determined during the course of analysis.

Preferably, there is at least one wavelet algorithm for de-noising the collected data to achieve the preset signal quality response function value (e.g. a pre-determined signal-to-noise ratio) at a reduced integration time. In an embodiment, the adaptive wavelet de-noising method of the invention allows for the choice of wavelet filter and thresholding/shrinking parameters to be optimized in real-time using criteria specified beforehand. Thus, criteria may be specified based on values obtained using reference spectra of known components. Alternatively, wavelet de-noising may be accomplished by optimizing the wavelet filter to obtain the required wavelet coefficients. For example, software can be programmed to search through a bank of available filters and options until a filter is found which meets some pre-determined signal quality response function (e.g., a signal to noise ratio, S/N, of 100).

After shrinkage, an inverse transform is preferably computed to produce a wavelet processed signal (53). The wavelet processed signal can then be tested to determine signal quality, as for example, by computing the improved S/N (54).

The next step (60) comprises an evaluation of whether the processed data satisfies the pre-determined signal quality response function value (e.g., S/N=20). In an embodiment, this step may be by-passed and samples analyzed for the parameter of interest (90). In an embodiment, samples for which wavelet processed signals that do not meet the pre-set signal quality response function value may be processed using a different algorithm characterized by a different combination of parameter settings or variation (decrease or increase) in the integration time (70). Preferably, the parameters of the wavelet transform algorithm are determined during the course of analysis. Thus, in an embodiment, the results from the (n) de-noising are used to evaluate parameters for the (n+1) de-noising, and results from the (n) and (n+1) de-noising are used to evaluate parameters for the (n+2) de-noising, and so on. In an embodiment, parameter settings, such as wavelet filter, number of vanishing moments, shrinkage method, low frequency cutoff, that produce the highest quality spectrum are chosen as optimal may be used as starting points for the analysis of other samples.

For the wavelet processed data that does meet the pre-set signal quality response function, the signal parameter of interest is quantified and stored for processing, chemometric analysis, and selection of those samples which appear to comprise the best candidates based on the reaction being assessed (90).

In an embodiment, each sample of a larger array is analyzed individually. Alternatively, samples comprising a multiple arrays (or multi-order arrays) (103) may be processed simultaneously (FIG. 3). For example, an entire multi-element array can be analyzed using imaging techniques such as, but not limited to: (a) the analysis of scattered, reflected, or transmitted light from samples irradiated with light from a light source; (b) the analysis of radiation emission from samples upon excitation with a source of electromagnetic or ionizing radiation; and (c) the analysis of thermal or luminescence radiation emitted from samples during a chemical reaction, mechanical testing, and the like. The array can be analyzed using sensor array techniques where each sample in the array is analyzed with an individual sensor or a sensor array and the data is collected from the sensors simultaneously.

In one aspect, the invention comprises an apparatus for analyzing a sample for at least one pre-selected spectroscopic or imaging property, which comprises: (a) a collecting system for collecting analytical data comprising the parameter of interest from the sample; (b) a processing system for processing the imaging or spectral data; (c) a screening rate accelerator toolbox for applying mathematical transform analysis to the data; (d) a data analysis system for determining whether the wavelet processed data satisfies the pre-determined signal quality response function; and (e) a statistical toolbox for analyzing the processed data for the parameter of interest.

Figure 4:
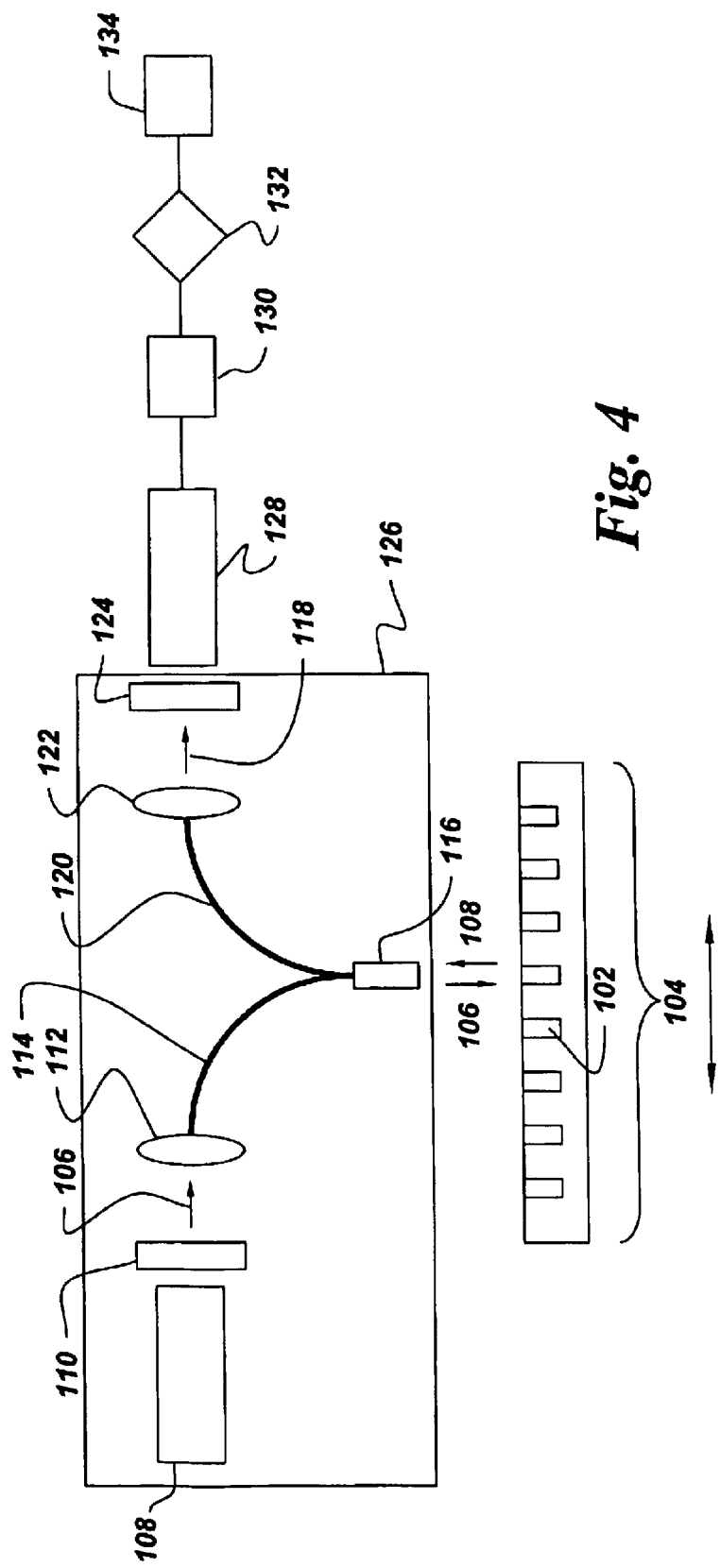
FIG. 4 illustrates an aspect of an embodiment of the apparatus of the invention comprising a system for serial screening of combinatorial libraries.
Figure 5:
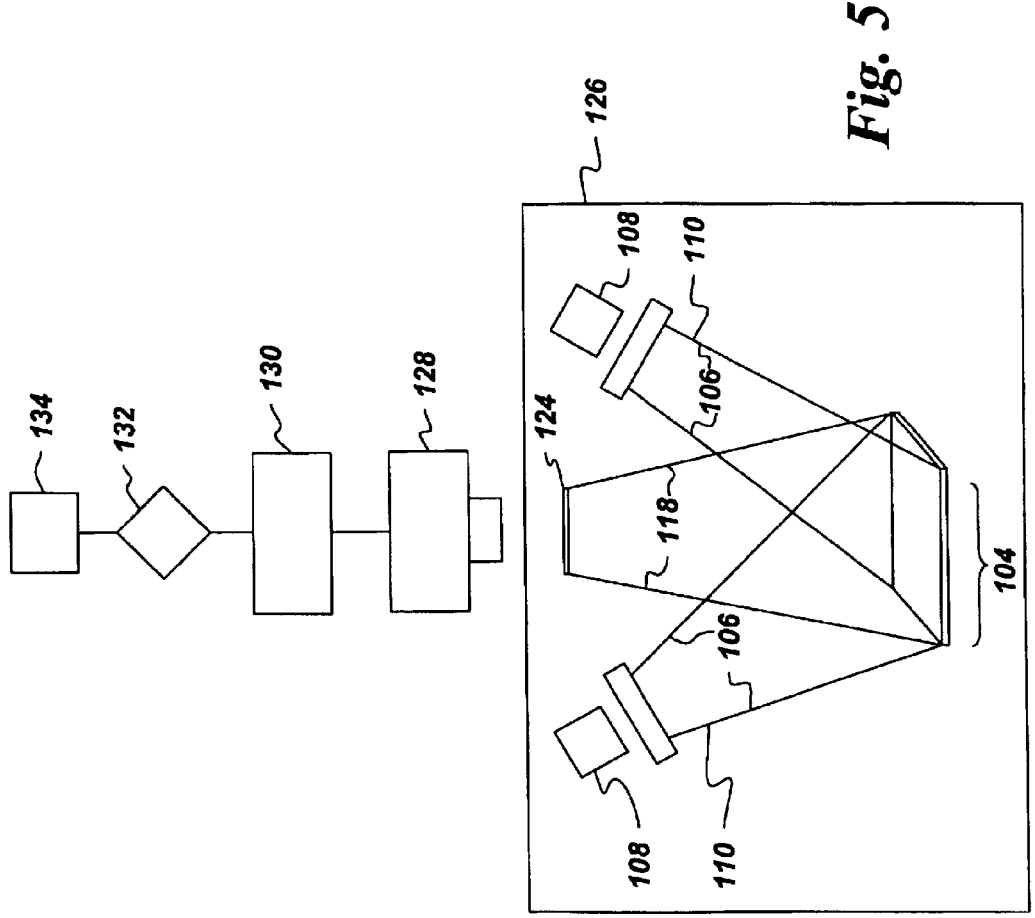
FIG. 5 illustrates an aspect of an embodiment of the apparatus of the invention comprising a system for parallel screening of combinatorial libraries.

Thus, referring now to FIGS. 4 and 5, the apparatus may comprise a sample array 104 where at least one well comprising individual sample 102 is analyzed using collecting system 126. In an embodiment, the sample 102 is irradiated with excitation light 106 generated from light source 108. Excitation light 106 can be filtered via wavelength selection component 110 prior to transmission via coupling optics component 112 and illuminating fiber optic cable 114 to probe 116 for irradiation of sample 102. Similarly, emitted radiation 118 collected by probe 116 passes via collecting fiber optics cable 120 through coupling optics component 122 and emission wavelength selection component 124 prior to processing by processing system 128. The signal is then transmitted for transformation using screening rate accelerator toolbox 130 and then processed by data analysis system 132 for selection of signals that satisfy a pre-determined signal quality response function value prior to processing by statistical toolbox 134 for analysis of the de-noised data for a parameter of interest.

In an embodiment, the apparatus is suited for analysis of individual sample wells (FIG. 4). In an embodiment, and referring now to FIG. 5, the apparatus is suited for simultaneous analysis of a multi-element array 104. For simultaneous analysis of a multi-element array 104, a single or multiple light source 108, with associated wavelength selectors 110 may be positioned at selected angles to illuminate an array 104 of samples with excitation light 106. Emitted radiation 118 is then transmitted to imaging detector 128, preferably after processing by wavelength selection component 124. The signal is then transmitted for wavelet processing by the screening rate accelerator toolbox 130 and then processed by data analysis system 132 for selection of signals that satisfy a pre-determined signal quality response function criteria prior to processing by statistical toolbox 134.

In some embodiments, the apparatus of the invention may not include a light source. For example, a light source is not required for measurement of luminescence emission or thermal emission from a sample or set of samples. Luminescence may occur during a chemical reaction, or as a result of a mechanical perturbation as in for example a performance test of solid material.

The screening rate accelerator toolbox may be applied to analysis of Raman or other spectral analysis. For example, Raman bands at 911 cm$^{-1}$ and 1072 cm$^{-1}$ can be used for the quantification of diphenyl carbonate (DPC), a starting component used in melt polymerization synthesis of polycarbonate. For Raman spectroscopic analysis of small-scale polycarbonate samples, however, detector integration time for unprocessed (original) spectra typically ranges from tens of seconds to several minutes for each sample. This can result in data acquisition times of several hours for even small (<1,000) combinatorial libraries of samples.

Figure 6:
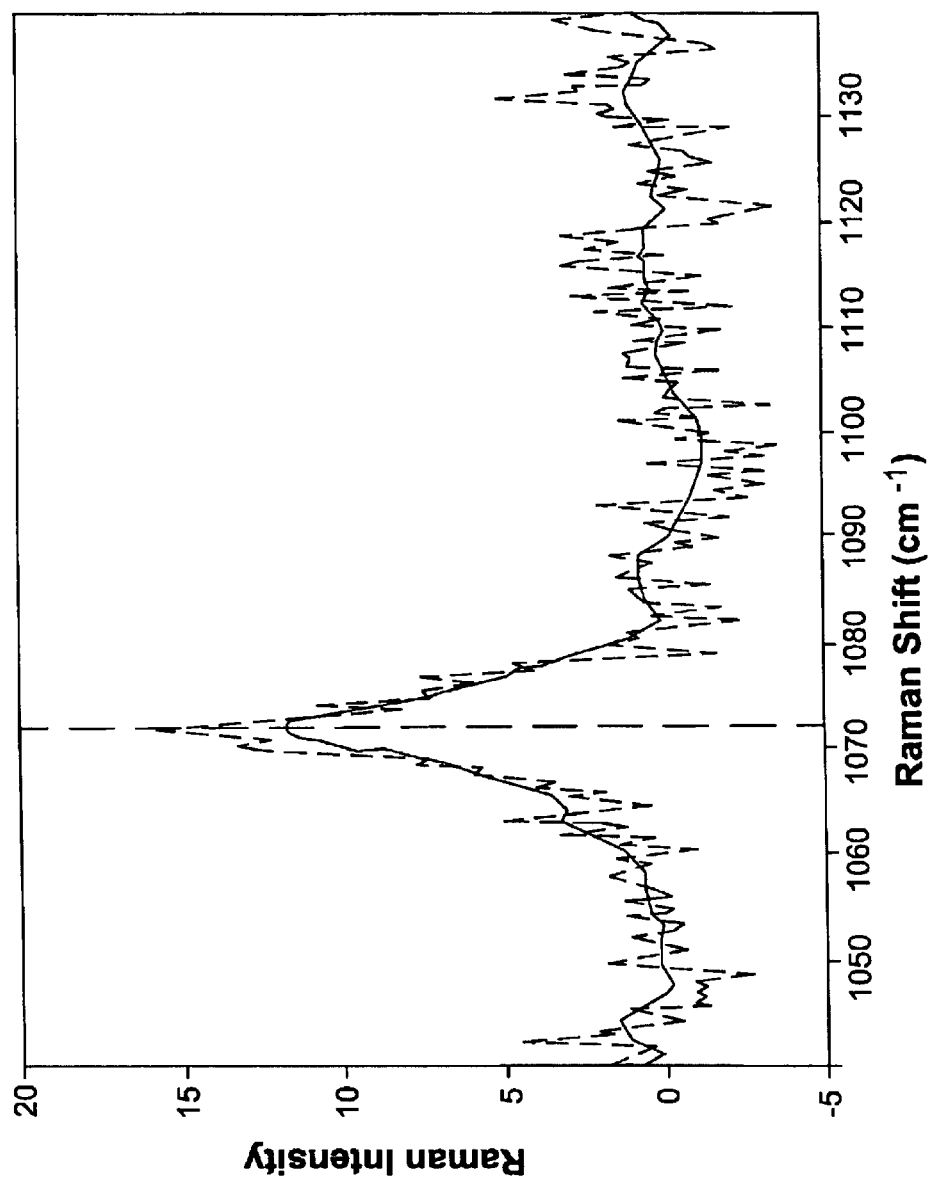
FIG. 6 illustrates an aspect of an embodiment of the invention showing an original spectrum (dotted line) and a wavelet processed spectrum (solid line) in the region of the 1072 $cm^{-1}$ band of a Raman spectrum of diphenyl carbonate (DPC) using the screening rate accelerator toolbox of the invention.
Figure 7:
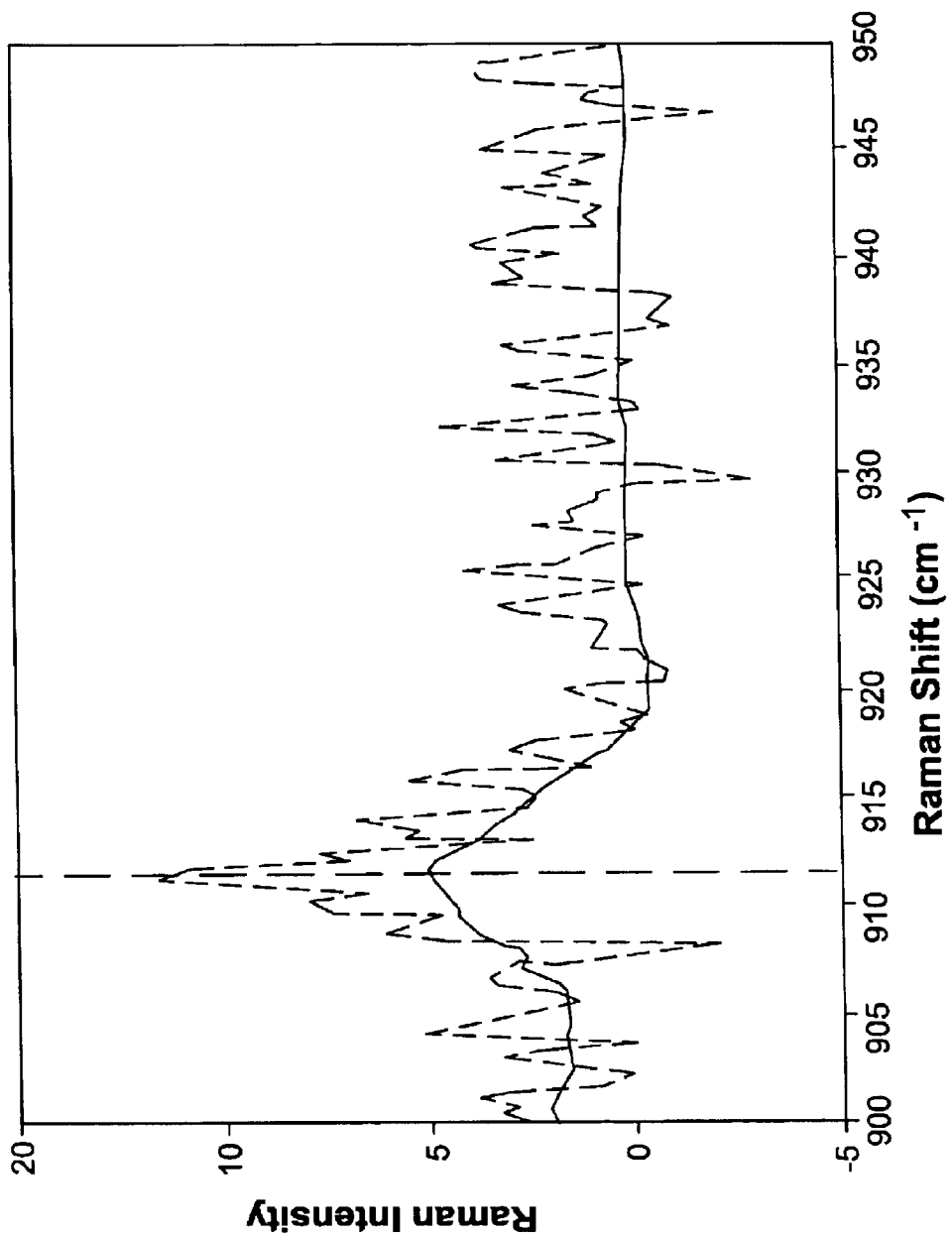
FIG. 7 illustrates an aspect of an embodiment of the invention showing an original spectrum (dotted line) and a wavelet processed spectrum (solid line) in the region of the 911 $cm^{-1}$ band of a Raman spectrum of diphenyl carbonate (DPC) using the screening rate accelerator toolbox of the invention.

For example, FIGS. 6 and 7 illustrate the signal-to-noise (S/N) improvements that result upon applying a screening rate accelerator toolbox comprising wavelet transform to de-noise Raman spectra of diphenyl carbonate (DPC), wherein the dashed lines correspond to the original spectra and the solid lines correspond to wavelet processed spectra, located near the 1072 cm$^{-1}$ and 911 cm$^{-1}$ peaks, respectively. In an embodiment, signal to noise enhancement may be determined by dividing the S/N of the spectra after de-noising by the S/N ratio of the original spectra.

The increased S/N resulting from the adaptive wavelet transform method of the invention can be used to decrease integration time. For example, referring now to FIG. 8, an original Raman spectra for the diphenyl carbonate 1072 cm$^{-1}$ band 144 achieves a maximal S/N value 140 at an integration time 142 of about 50 to 900 seconds. For the wavelet transformed spectra 146, this same S/N is obtained after an integration time 142 of 5 seconds, thus allowing for a relative improvement in integration time ($T_b/T_a$) by at least factor of 10 and a $\Delta T$ of at least 45 seconds per sample (horizontal arrow). Referring now to FIG. 9, for untransformed the 911 cm$^{-1}$ diphenyl carbonate band 150, the maximum S/N value 140 is obtained after an integration time 142 of 900 seconds. For the wavelet transformed spectra 152 this S/N value 140 is obtained after an integration time 142 of 10 seconds, thereby resulting in a relative improvement in integration time ($T_b/T_a$) by about 90-fold and a $\Delta T$ of about 890 seconds per sample (horizontal arrow).

In an embodiment, the reduction in integration time $\Delta T$ is a function of the pre-determined signal quality response function of interest. Where S/N is the signal quality response function of interest, the reduction in integration time $\Delta T$ generally increases as the S/N function value is increased. The increase may be linear (FIG. 10) or may plateau at higher S/N values (FIG. 11). Thus, for measurements requiring highly stringent criteria (e.g. a high S/N), the method of the present invention may save significant amounts of integration time per sample.

The reduction in signal integration time upon applying the screening rate accelerator toolbox of the present invention correlates to a overall reduction in data acquisition time. In an embodiment, the screening rate accelerator toolbox of the invention can dramatically reduce integration time per sample, and is particularly useful for libraries having multiple samples, each requiring integration times exceeding about 10 msec. FIG. 12 shows the amount of time saved for screening combinatorial libraries ranging from 10 to 5,000 diphenyl carbonate samples when the screening rate accelerator toolbox of the invention is applied.

Other types of spectroscopic measurements are suitable for the methods of the present invention. Also, the sample may be inorganic material, organic material, polymeric material, biological material, or combinations thereof. For example, the screening rate accelerator toolbox of the present invention has been applied to reduce sample integration time for light scattering measurements at 500 nanometers (nm) of combinatorial libraries of protective organic hard coatings. In an embodiment, wavelet processing by the method of the invention de-noises the spectra so that a predetermined S/N ratio (S/N=25) is found with a lower integration time for wavelet processed measurements (i.e. 50 msec) as opposed to non-processed measurements (i.e. 500 msec), thus, resulting in a 20-fold reduction in integration time, and an overall savings in time of 450 msec/sample. Time savings on a msec scale can be important for monitoring of rapid dynamic processes important in such fields as medicine, rapid reaction kinetics, physics, biology, and the like.

As will be recognized by those of ordinary skill in the art, all or part of the steps in the method of the present invention may be coded or otherwise written in computer software, in a variety of computer languages including, but not limited to, C, C++, Pascal, Fortran, Visual Basic, Microsoft Excel, MATLAB, Mathematica, Java, and the like. Accordingly, additional aspects of the present invention include computer software for performing one or more of the method steps set forth herein. The software code may be compiled and stored in executable form on computer readable media as, for example, computer ROM, floppy disk, optical disk, hard disks, CD ROM, or the like. The invention may be further understood by reference to the following non-limiting examples.

EXAMPLE 1

Raman spectroscopy can be used for the high throughput screening of combinatorial libraries. Integration time for Raman spectroscopy, however, is dependent on sample size. For samples ranging from 10 mL to 0.01 mL (the size used for combinatorial analysis), integration time typically ranges from tens of seconds to several minutes. Thus, to achieve the high throughput of multiple samples, it is important to decrease the integration time required for acquisition of data while maintaining a S/N which allows for quantification of the reaction components of interest.

The production of polycarbonate by melt polymerization utilizes diphenyl carbonate (DPC) and bis-phenol A (BPA). Monitoring the ratio of these two starting components can be useful for optimizing the overall reaction. In this example, Raman bands at 911 $cm^{-1}$ and 1072 $cm^{-1}$ were used for quantification of sample DPC.

Measurements were performed using a fiber-optic Raman system that consisted of a spectrograph, a laser, and a fiber-optic probe. The Raman spectrograph (Model Echell-NIR775; EIC Raman Systems, Norwood, Mass.) covered a spectral range from 200 to 3500 $cm^{-1}$ with a 4 $cm^{-1}$ resolution. This capability was available by using a gold-coated echelle grating (52.65 lines/mm) that dispersed light in two dimensions to fully exploit the CCD detector area. The detector was a cryogenically cooled CCD camera (Model CH270, Photometrics Inc.; Tuscon, Ariz.). The light source was a wavelength-stabilized high-power diode laser (300 mW output power, 785 nm emission wavelength, Model SDL-8530; SDL Inc., San Jose, Calif.). Raman spectra were collected using a data acquisition package (EIC Raman Systems; Norwood, Mass.) and converted into ASCII format using GRAMS/32 software (Galactic Industries, Inc., Salem, N.H.). Raman spectra were collected using a standard 5 m long fiber-optic sampling probe (EIC Raman Systems; Norwood, Mass.).

A sample of DPC was measured at 13 different integration times (0.1, 1, 5, 10, 30, 60, 120, 180, 240, 300, 420, 600, and 900 seconds) resulting in a total of 13 spectra for analysis. A reference spectrum of the chemical system under study (in this case DPC) was used to select baseline regions where no analyte exists and to find spectral regions specific to DPC. Bands at 911 and 1072 $cm^{-1}$ bands were selected. Thus, for measurements of DPC samples, spectra were truncated to a total of 1024 points covering the spectral region between 800 $cm^{-1}$ and 1200 $cm^{-1}$.

The signal quality response function, y=f(x), used in this example consisted of the signal-to-noise ratio (S/N), which was determined by dividing the signal (intensity at 911 or 1072 $cm^{-1}$) by the noise (root-mean square intensity between 930 and 950 $cm^{-1}$ for the 911 $cm^{-1}$ band and between 1090 and 1140 for the 1072 $cm^{-1}$ band).

Adaptive wavelet de-noising algorithms using multiple different combinations of Daubechies and Symmlet wavelet filters and threshold/shrinkage options were used to maximize S/N for each spectrum. Wavelet de-noising was performed in the MATLAB™ programming environment (Mathworks, Inc., Natick, Mass., Version 5.3) using functions written internally and from the Stanford University WAVELAB™ toolbox (http://www-stat.stanford.edu/~wavelab, Version 8.02). For the 13 spectra analyzed in this example, a majority of the optimized wavelets used four vanishing moments for the Daubechies filter, and eight vanishing moments for the Symmlet filters. It is to be understood that in an alternative embodiment, software which searches through a bank of available filters and options until one or combination of filters/options is found which meets a pre-determined signal quality function (e.g. y=S/N of 20) can be used for selection of the appropriate algorithm parameters.

A threshholding procedure was then applied to the wavelet coefficients to reduce or remove those wavelet coefficients which were mainly due to noise. In this example, soft thresholding or wavelet shrinking methods which reduce the value of wavelet coefficients caused by noise were optimized by varying both the shrinkage method, and the low frequency cutoff each spectrum. Generally, shrinkage methods such as 'Visu', 'SURE', and 'MAD' with low-frequency cutoffs between 2 and 6 were found to be satisfactory for this application (see e.g., D. L. Donoho and I. M. Johnstone, the WAVELAB™ toolbox at http://www-stat.Stanford.edu/~wavelab).

After application of each shrinkage method, an inverse transform was used to produce a wavelet processed spectrum. The spectra were then tested to determine their signal quality response value, y. The parameter settings (i.e., wavelet filter, number of vanishing moments, shrinkage method, and low frequency cutoff) that produced the highest quality spectrum (in this example, highest S/N) were chosen as optimal. The optimization procedure was repeated for each of the 13 Raman spectra collected at the different integration times.

FIGS. 6 and 7 illustrate the S/N improvements that result upon applying the screening rate accelerator toolbox to Raman spectra of melt polycarbonate at the 1072 cm–1 and 911 cm–1 bands, respectively. In these figures, the dashed lines are the original spectra, and the wavelet processed spectra are shown as the solid lines. The dashed vertical line indicates the position of the peak of interest used for determination of S/N. Signal-to-noise enhancement was determined by dividing the S/N of the spectra after wavelet processing by the S/N ratio of the original spectra. The improvement in S/N comprises a factor of 13.2 for the 1072 $cm^{-1}$ band (FIG. 6), and a factor of 2.8 for the 911 $cm^{-1}$ band (FIG. 7).

Figure 8:
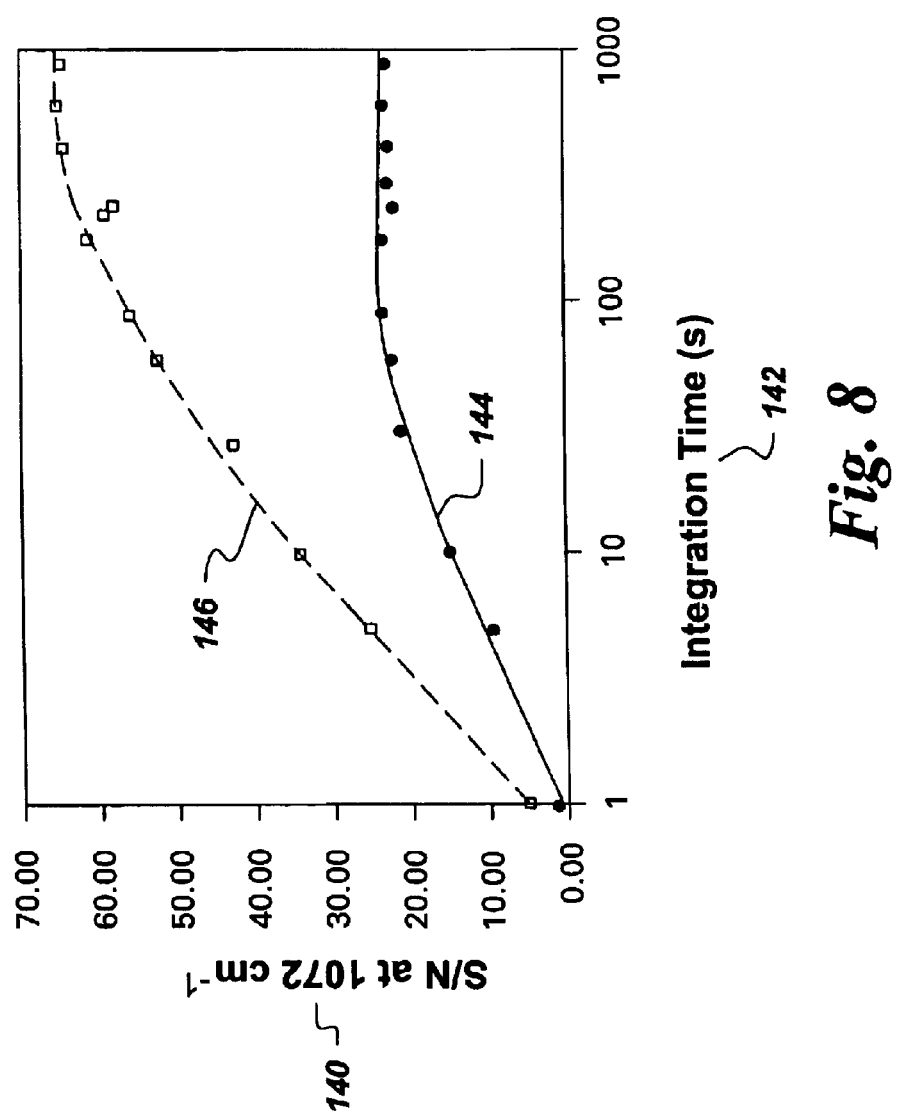
FIG. 8 illustrates an aspect of an embodiment of the invention comprising a reduction in integration time for Raman analysis of diphenyl carbonate (DPC) at the 1072 $cm^{-1}$ band where solid circles are before, and open squares are after, signal processing by the method of the invention.
Figure 9:
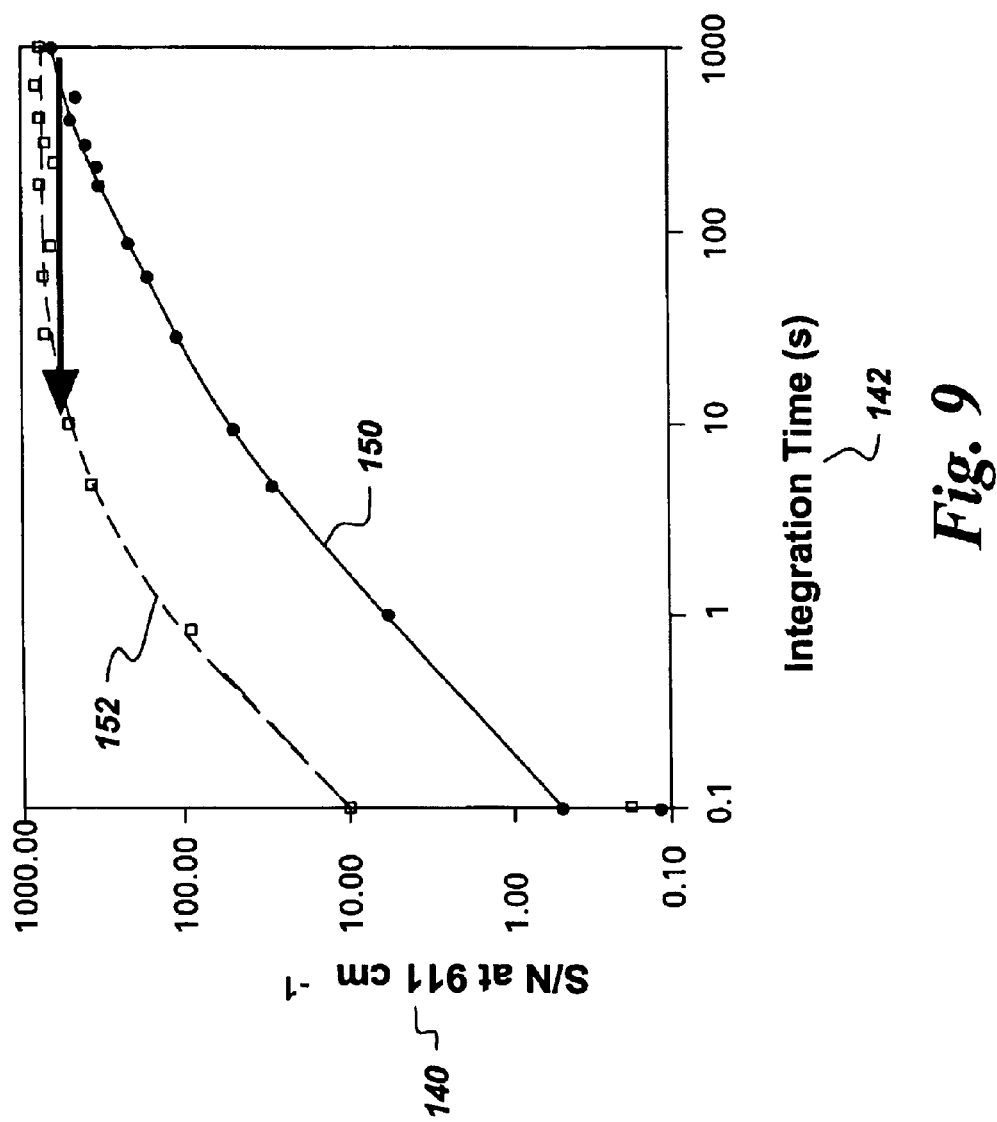
FIG. 9 illustrates an aspect of an embodiment of the invention comprising a reduction in integration time for Raman analysis of diphenyl carbonate (DPC) at the 911 cm$^{-1}$ band where solid circles are before, and open squares are after, signal processing by the method of the invention.

FIGS. 8 and 9 show the signal-to-noise (S/N) ratios as a function of integration time for the 1072 $cm^{-1}$ and 911 $cm^{-1}$ bands before (solid circles) and after (open squares) wavelet processing of the data. The increased S/N resulting from the adaptive wavelet de-noising method of the invention can be used to decrease integration time. For the original, unfiltered spectra, the maximal S/N for the 1072 $cm^{-1}$ band was obtained after a 50 to 900 second integration time (FIG. 8). For the wavelet processed spectra, this same or higher level of S/N was obtained at integration times of 5 seconds, thus resulting in an at least 10 to 180 fold decrease in integration time. For the 911 cm$^{-1}$ band, the original spectra had a maximum S/N at 900 second integration time. For the wavelet processed spectra, an equivalent S/N value was obtained after 10 second integration time, thus resulting in a 9 fold decrease in integration time (FIG. 9).

As shown in FIGS. 10 and 11, it was found that there is a significant reduction of signal integration time at each S/N when the screening rate acceleration toolbox of the invention is applied to the spectra. The plots shown in these two figures were generated (from FIGS. 8 and 9, respectively) by subtracting the value of the integration time for the original (unprocessed) spectra from the integration time upon applying the screening rate accelerator toolbox for a given signal-to-noise ratio (S/N) for the corresponding spectra. Notably, there was a significant increase for the reduction in the integration time $\Delta T$ with an increase in S/N (FIGS. 10 and 11). For example, for the 1072 cm$^{-1}$ band, to achieve a S/N ratio of 20 required about 147 seconds integration time for the unprocessed spectra, but only 3 seconds for the wavelet processed data, thereby resulting in a savings of about 144 seconds of integration time per sample (FIG. 10). For the 911 cm$^{-1}$ band, the time saved for a S/N=20 is on the order of 10 seconds per sample (FIG. 11).

EXAMPLE 2

FIG. 12 depicts the total time required to screen libraries of different size before, and after, application of the screening rate accelerator toolbox of the invention. In this example, a preset S/N value of 20 was selected as the S/N value required to achieve necessary precision and accuracy of analysis for the 1072 cm$^{-1}$ DPC Raman band. It was found that to achieve a S/N value of 20, the unprocessed (original) spectra had to be integrated for 147 seconds (about 2.5 min). Using the screening rate accelerator toolbox of the present invention, the same quality of spectrum (S/N=20) is achieved with an integration time of 3 seconds (a 50-fold decrease). This savings of 144 seconds per sample provides a total time savings per library as shown, where the open circles correspond to the total analysis time for a given library of original spectra before, and the closed circles correspond to the total analysis time for a given library after, application of the screening rate accelerator toolbox of the invention.

It will be recognized by those in the art that advantages of wavelet transform analysis to reduce data acquisition time disclosed here over other methods for the screening of potential reaction conditions include:

1. An increase in screening throughput of 10–200 times using exclusively software tools;
2. A method for rapid, real-time assessment of multiple reactions;
3. Safe, non-invasive measurements;
4. Measurement of small reaction volumes;
5. High-throughput, rapid analysis capable of automation for combinatorial chemistry or production-scale applications;
6. Analysis of gaseous, dissolved, solid or molten samples;
7. Application to a large variety of spectroscopic and imaging techniques;
8. Samples may be inorganic, organic, polymeric or biological; and
9. Measurements may detect from a single molecule to components making up 100% of the sample.

It will be understood that each of the elements described above, or two or more together, may also find utility in applications differing from the types described herein. While the invention has been illustrated and described as a method for rapid, high-throughput, nondestructive analysis of combinatorial reactions, it is not intended to be limited to the details shown, since various modifications and substitutions can be made without departing in any way from the spirit of the present invention. For example, robotics equipment can be used to prepare the samples, and various types of parallel analytical screening methods can be incorporated. Also, other parameters besides Raman analysis of diphenyl carbonate and light scattering measurements of sample hazing can be measured. As such, further modifications and equivalents of the invention herein disclosed may occur to persons skilled in the art using no more than routine experimentation, and all such modifications and equivalents are believed to be within the spirit and scope of the invention as defined by the following claims.

We claim:

1. A method for reducing the time required for analyzing at least one sample for a parameter of interest which comprises:

selecting a pre-determined signal quality response function value;

selecting a pre-determined integration time $T_a$;

collecting analytical data from a sample with integration time $T_a$;

determining whether the analytical data collected from the sample with integration time $T_a$ satisfies the pre-determined signal quality response function value prior to applying a screening rate accelerator toolbox;

applying the screening rate accelerator toolbox if the collected data does not satisfy the predetermined signal quality response function value.

said screening rate accelerator toolbox comprising mathematical transform analysis to the data, wherein the mathematical transform analysis is performed using conditions designed to achieve the pre-determined signal quality response function value comprising the value obtained when samples are analyzed without mathematical transform analysis using integration time $T_b$, wherein $T_b$ is greater than $T_a$; and analyzing the data processed by the screening rate accelerator toolbox for the parameter of interest.

2. The method of claim 1, wherein the mathematical transform analysis comprises multivariate analysis.

3. The method of claim 2, wherein the multivariate analysis comprises neural networks analysis, principal components analysis, partial least squares analysis, linear multivariate analysis, or nonlinear multivariate analysis.

4. The method of claim 1, wherein the mathematical transform analysis comprises discrete transform analysis.

5. The method of claim 1, wherein the mathematical transform analysis comprises continuous transform analysis.

6. The method of claim 1, wherein the mathematical analysis comprises time averaging analysis, smoothing analysis or Savitsky-Golay analysis.

7. The method of claim 1, wherein the mathematical transform analysis comprises Fourier transform, Gabor transform, or Hadamard transform.

8. The method of claim 1, wherein the mathematical transform analysis comprises wavelet transform.

9. The method of claim 8, wherein the wavelet transform analysis comprises a wavelet de-noising algorithm.

10. The method of claim 9, wherein the wavelet de-noising algorithm comprises wavelet filters.

11. The method of claim 9, wherein the wavelet de-noising algorithm comprises a threshold/shrinkage method.

12. The method of claim 1, wherein parameters of the mathematical transform are determined during the course of analysis.

13. The method of claim 1, further comprising the steps of:
   determining whether the data processed by the screening rate accelerator toolbox satisfies the pre-determined signal quality response function value; and
   if the processed data does not satisfy the pre-determined signal quality response value, re-applying the screening rate accelerator toolbox using a mathematical transform analysis different from the analysis previously applied until the data processed using the screen rate accelerator toolbox either satisfies the pre-determined signal quality response function value or comprises an optimized signal quality response function value.

14. The method of claim 13, further comprising repeating the method with a new, larger value for $T_a$ if the data which is optimized using the screening rate accelerator toolbox does not satisfy the pre-determined signal quality response function value.

15. The method of claim 1, wherein if the collected data does not require application of the screening rate accelerator toolbox to satisfy a pre-determined signal quality response function value, a shorter pre-determined integration time $T_a$ is selected, and the method is performed using the new value for $T_a$.

16. The method of claim 1, wherein the predetermined signal quality response function comprises one or more measured signal parameters.

17. The method of claim 16, wherein at least one of the measured signal parameters comprises signal resolution.

18. The method of claim 16, wherein at least one of the measured signal parameters comprises peak shift.

19. The method of claim 16, wherein at least one of the measured signal parameters comprises signal distortion.

20. The method of claim 16, wherein at least one of the measured signal parameters comprises a signal-to-noise ratio.

21. The method of claim 20, wherein the signal to noise ratio ranges from 1 to about 10,000.

22. The method of claim 20, wherein the signal to noise ratio ranges from 2 to 5,000.

23. The method of claim 20, wherein the signal to noise ratio ranges from 3 to 1,000.

24. The method of claim 1, wherein the relative improvement in signal integration time $(T_b/T_a)$ ranges from about 1.5 to 1,000 fold.

25. The method of claim 1, wherein the relative improvement in signal integration time $(T_b/T_a)$ ranges from about 1.5 to 500 fold.

26. The method of claim 1, wherein the relative improvement in signal integration time $(T_b/T_a)$ ranges from about 1.5 to 200 fold.

27. The method of claim 1, wherein the analytical data comprises a first-order array.

28. The method of claim 1, wherein the analytical data comprises a multi-order array.

29. The method of claim 1, further comprising simultaneous evaluation of each individual sample in an array of samples.

30. The method of claim 1, wherein the analytical data comprise spectroscopic, imaging, sensor, or scanning data.

31. The method of claim 30, wherein the data further comprise measurements made using Raman, luminescence, ultraviolet-visible molecular absorbance, atomic absorbance, infra-red, near infrared, surface plasmon resonance, mass spectrometry, X-ray, nuclear magnetic resonance, refractometry, interferometry, scattering, inductively coupled plasma, atomic force microscopy, scanning tunneling microscopy, microwave evanescent wave microscopy, near-field scanning optical microscopy, atomic fluorescence, laser-induced breakdown spectroscopy, Auger electron spectroscopy, X-ray photoelectron spectroscopy, ultrasonic spectroscopy, dielectric spectroscopy, microwave spectroscopy, resonance-enhanced multiphoton ionization, or combinations thereof.

32. The method of claim 30, wherein the data further comprise measurements made using photon probe microscopy, electron probe microscopy, ion probe microscopy, field probe microscopy, or scanning probe microscopy techniques.

33. The method of claim 1, wherein analytical data is provided using techniques relying on collection of electromagnetic radiation in the range from 0.05 Angstroms to 500 millimeters (mm).

34. The method of claim 1, wherein the sample comprises inorganic material, organic material, polymeric material, biological material, or combinations thereof.

35. The method of claim 1, wherein the parameter of interest ranges from a single molecule to up to 100% of the sample.

36. The method of claim 1, wherein the sample comprises polycarbonate.

37. Computer readable media comprising software code for performing the method of claim 1.

* * * * *

UNITED STATES PATENT AND TRADEMARK OFFICE
CERTIFICATE OF CORRECTION

PATENT NO.    : 6,763,322 B2
DATED         : July 13, 2004
INVENTOR(S)   : Radislav Alexandrovich Potyrailo et al.

It is certified that error appears in the above-identified patent and that said Letters Patent is hereby corrected as shown below:

<u>Column 22,</u>
Line 37, please replace "." with -- , --

Signed and Sealed this

Seventh Day of December, 2004

JON W. DUDAS
*Director of the United States Patent and Trademark Office*